United States Patent [19]

Yamamoto et al.

[11] Patent Number: 5,506,120
[45] Date of Patent: Apr. 9, 1996

[54] METHOD OF PRODUCING PEPTIDES OR PROTEINS AS FUSION PROTEINS

[75] Inventors: Hiroaki Yamamoto; Kunihiko Yamashita, both of Tsukuba, Japan

[73] Assignee: M & D Research Co., Ltd., Tokyo, Japan

[21] Appl. No.: 243,082

[22] Filed: May 16, 1994

Related U.S. Application Data

[63] Continuation of Ser. No. 853,754, Jun. 5, 1992, abandoned.

[30] Foreign Application Priority Data

Oct. 9, 1990 [JP] Japan ................................. 2-271880

[51] Int. Cl.⁶ .................................................. C12N 15/62
[52] U.S. Cl. ..................... 435/69.7; 435/64.1; 435/752.3; 435/320.1; 435/69.3; 435/69.4; 435/69.6; 435/69.2; 435/69.5; 435/69.8; 536/23.4
[58] Field of Search ................................ 435/69.1, 69.7, 435/212, 252.3, 320.1; 536/23.4, 23.5

[56] References Cited

U.S. PATENT DOCUMENTS

| | | | |
|---|---|---|---|
| 4,828,994 | 5/1984 | Fahnestock et al. | 435/172.3 |
| 5,053,333 | 10/1991 | Yamamoto | 435/212 |

FOREIGN PATENT DOCUMENTS

| | | |
|---|---|---|
| 0001930 | 5/1979 | European Pat. Off. . |
| 35384 | 9/1981 | European Pat. Off. . |
| 0163406 | 4/1985 | European Pat. Off. . |
| 0150126 | 7/1985 | European Pat. Off. . |
| 196056 | 10/1986 | European Pat. Off. . |
| 0312346 | 4/1989 | European Pat. Off. . |
| 327377 | 8/1989 | European Pat. Off. . |
| 63-71195 | 3/1988 | Japan . |
| 1-191683 | 8/1989 | Japan . |
| 2-271880 | 2/1994 | Japan . |
| 8403103 | 8/1984 | WIPO . |

OTHER PUBLICATIONS

Eur. J. Biochem 170: 241–246, (1987) Van Den Bergl et al Secretion of Biologically Active Porcine Prophoshpholipase AL by *Saccharomyces cerevisiae*.
Gone 61: 103–112, 1987, Lennich et al. High–Level Expression of α–Human Atrial Natriuretz Peptide from Multiple Genes in *Eschericia coli*.
Andras Simoncsits et al., "Synthesis, cloning and expression in *Escherichia coli* of artificial genes . . . " *European Journal of Biochemistry*, vol. 178, No. 2, pp. 343–350 (1988).
Gluschankof, et al., "Enzymes That Process Somatostatin Precursors", *The Journal of Biological Chemistry*, vol. 262, No. 20, pp. 9615–9620 (1987).
Sugimara, et al., "Purification, Characterization, and Primary Structure of *Escherichia coli* Protease VII with Specificity for Paired Basic Residues: Identity of Protease VII and OmpT", *Journal of Bacteriology*, vol. 170, No. 12, pp. 5625–5632 (1988).

*Primary Examiner*—Garnette D. Draper
*Assistant Examiner*—John D. Ulm
*Attorney, Agent, or Firm*—Spencer & Frank

[57] ABSTRACT

A fusion protein comprising a carrier and a desired peptide or protein linked to the carrier via an enzymatically excisable dipeptide, such as Lys-Arg, is produced in a host microorganism and then the desired peptide or protein is recovered by treating the fusion protein at least with a protease specifically recognizing the dipeptide and specifically hydrolyzing the peptide bond of the dipeptide. The fusion protein includes tandem-form fusion proteins in which desired peptide or protein molecules are linked together repeatedly. According to the cleavage site in the dipeptide, the protease may be used in combination with an aminopeptidase specifically releasing a basic amino acid from the N-terminal side of the dipeptide and/or a carboxypeptidase specifically releasing a basic amino acid from the C-terminal side of the dipeptide.

25 Claims, 6 Drawing Sheets

METHOD OF PRODUCING PEPTIDES OR PROTEINS AS FUSION PROTEINS

This application is a continuation of application Ser. No. 07/853,754, filed Jun. 05 1992, now abandoned, which was the national stage of International Application PCT/JP91/00239, filed Feb. 25 1991, which claims priority to Japanese Application No. 271880/1990, filed Oct. 09 1990, the specifications of which are hereby incorporated by reference.

TECHNICAL FIELD

The present invention relates to a method of producing peptides or proteins which comprises causing a host to produce a peptide or protein as a fusion protein by utilizing recombinant DNA techniques and treating the fusion protein with a protease specific thereto to produce the peptide or protein as such.

BACKGROUND ART

Utilization of the recombinant DNA technology in an attempt to produce heterologous peptides or proteins fails in large-scale production in many instances even in the case of direct expression of the desired gene products. As for the reasons therefor, it has been pointed out, for instance, that the translation initiation reaction on the genes to be expressed is inhibited by the influence of the higher-order structure of mRNA in the vicinity of the initiation codon [D. Iserentant, E. Fiers, Gene, 9, 1 (1980)] and that when the desired gene products have a low molecular weight, they are readily degraded particularly by host-derived proteases.

The fusion protein method has now attracted attention as a method capable of solving these problems. In this fusion protein method, desired peptides or proteins are produced in a form fused with a carrier, for example a peptide or protein, which is stable in the host and is produced in large quantities. This fusion protein method includes those cases as well in which carriers don't come under the category of proteins in general, namely carriers composed of less than 50 amino acid residues. Even in the case of direct expression as fusion proteins, the processing by methionine amino-peptidase in the host is incomplete, so that the methionine residue derived from the initiation codon is not fully eliminated but partly remains, giving, in many instances, the desired gene products with methionine added to the N terminus thereof. A possibility has been pointed out that such gene products with said methionine added may have an antigenicity problem (Japanese Patent Laid-open No. 171699/1987). Therefore, for obtaining desired peptides or proteins from such fusion proteins or methionine-retaining gene products, it is necessary to excise the desired portions from the fusion proteins or such gene products. Chemical and enzymatic methods are known for this excision.

Chemical methods that are known include, for example, the cleavage of the peptide bonds on the C-terminal side of Met by cyanogen bromide [D. V. Goeddel et al., Proc. Natl. Acad. Sci. USA, 76, 106–110 (1979)], the cleavage of the peptide bonds on the C-terminal side of Trp by BNPS-skatole or N-chlorosuccinimide (NCS) [Y. Saito et al., J. Biochem., 101, 123–134 (1987)], the cleavage of the peptide bond between Asp-Pro by an acid, for example, 70% formic acid or the like [Biochem. Biophys. Res. Commun., 40, 1173 (1970)], and the cleavage of the peptide bond between Asn-Gly by hydroxylamine.

However, because of strong dependency on the structure of each substrate fusion protein, the cleavage reactions, except for the cleavage by cyanogen bromide, give low yields and readily lead to side reactions. The cleavage with cyanogen bromide is widely used but cannot be applied to the cases where the desired gene products contain Met. When the amino acid next to Met is Ser or Thr, the cleavage reaction with cyanogen bromide scarcely proceeds in some instances. When the cleavage is effected between Asp-Pro or Asn-Gly bond, both the N-terminal and C-terminal sides of the peptides or proteins resulting from the cleavage have one or more remaining amino acids, so that it is difficult to obtain gene products having desired amino acid sequences at the N and C termini by cleavage.

Enzymatic methods that are known include, among others, the cleavage using a protease showing strict primary specificity, namely specificity to an amino acid just before (P1 position) or behind (P1' position) the peptide bond to be cleaved, for example the cleavage of the peptide bond on the C-terminal side of Arg or Lys by trypsin or a trypsin-like enzyme such as endoproteinase Arg-C [J. Shine et al, Nature, 285, 456–461 (1980)], the cleavage of the peptide bond on the C-terminal side of Lys by lysyl endopeptidase or endoproteinase Lys-C (Japanese Patent Laid-open No. 275222/1986), and the cleavage of the peptide bond on the C-terminal side of Glu or Asp by an enzyme specific to acidic amino acids, for example V8 protease (Japanese Patent Laid-open No. 501391/1985).

Generally, however, these Proteases are effective only when any amino acid recognized by them is not contained in the desired gene products. Therefore they are applicable only to a very limited range of gene products.

Not only enzymes showing primary specificity but also enzymes showing strict secondary specificity, namely specificity to sequence around the peptide bond to be cleaved, are in use. For example, reports are available on the cleavage of the peptide bond between X-Gly of chicken pro α-2 Collagen or Pro-X-Gly-Pro (SEQ ID NO: 17) by a collagenase [Japanese Patent Publication No. 44920/1987; J. Germino et al., Proc. Natl. Acad. Sci. USA, 81, 4692–4696 (1984)], the cleavage of the peptide bond on the C-terminal side of Ile-Glu-Gly-Arg (SEQ ID NO: 20) by blood coagulation factor Xa (Japanese Patent Laid-open No. 135591/1986), the cleavage of the peptide bond on the C-terminal side of Gly-Pro-Arg etc. by thrombin (Japanese Patent Laid-open No. 135500/1987), the cleavage of the peptide bond on the C-terminal side of Phe-Arg with kallikrein (Japanese Patent Laid-open No. 248489/1987), the cleavage of the peptide bond on the C-terminal side of Val-Asp-Asp-Asp-Asp-Lys (SEQ ID NO: 21) by entero-peptidase [T. P. Hopp et al., Biotechnology, 6, 1204–1210 (1988); Japanese Patent Laid-open No. 166200/1981], the cleavage of the peptide bond between Leu-Leu of Pro-Phe-His-Leu-Leu-Val-Tyr (SEQ ID NO: 22) by renin (Japanese Patent Laid-open No. 262595/1985), the cleavage of the peptide bond on the C-terminal side of poly-Gly by lysostaphin (Japanese Patent Laid-open No. 160496/1989), the cleavage of the peptide bond on the C-terminal side of ubiquitin by ubiquitin-$N^\alpha$-protein hydrolase [T. R. Butt et al., Proc. Natl. Acad. Sci. USA, 86, 2540–2544 (1989)], and the cleavage of the peptide bond on the C-terminal side of Glu-Gly-Arg by urokinase (Japanese Patent Laid-open No. 100685/1990).

However, the digestion with collagenase or renin allows peptides to remain on both the N-terminal and C-terminal sides of the cleavage site and therefore makes it difficult to obtain gene products having the desired amino acid sequences. It is reported that many enzymes, in particular thrombin, cause cleavage also at other sites than recognition sequences and are lacking in general-purpose property because of their low specificity [e.g. J. Y. Chang, Eur. J. Biochem., 151, 217–224 (1985)]. Blood coagulation factor Xa is currently in widest use for excising desired gene products from fusion proteins. Cases are, however, reported in which it cleaves other sites than specific recognition sequences as well, so that desired gene products cannot be obtained [e.g. S. Nishikawa et al., Protein Engineering, 1, 487–492 (1987)]; hence factor Xa is lacking in general-purpose property. For instance, when blood coagulation factor Xa or kallikrein is used for the excision of vasoactive intestinal polypeptide (hereinafter abbreviated as VIP) derivative as the desired gene products from fusion proteins, cleavage occurs within VIP, for example between $Arg^{14}$-Lys, so that no VIP can be obtained. Furthermore, these proteases are required in considerable quantities, for example 0.1 to 0.001 mole, generally about 0.01 mole, per mole of substrate fusion protein.

Another method of producing desired gene products is also known which comprises joining a carrier sequence to a DNA sequence coding for a desired gene via a sequence coding for a processing signal which is a dipeptide, thus producing a fusion protein, and enzymatically cleaving the dipeptide. Thus, reports are available on the production of desired gene products utilizing such dipeptide, in particular a pair of basic amino acid residues, for example the secretory production of desired gene products using the preproleader sequence (containing Lys-Arg) of α mating factor produced by *Saccharomyces cerevisiae* (Japanese Patent Laid-open No. 132892/1984) and the secretory production of desired gene products utilizing the preproleader sequence of α mating factor of *Kluyveromyces lactis* (Japanese Patent Laid-open No. 124390/1989). In these methods, fusion proteins undergo limited proteolysis in vivo and desired gene products are secreted extracellularly.

However, these methods are only applicable to those cases in which specific hosts, for example *Saccharomyces cerevisiae*, *Kluyveromyces lactis* and the animal cell line AtT-20, which possess processing systems for basic amino acid pair cleavage, secretion, glycosylation and so forth; hence, they are not generally applicable methods. The use of these systems results in various problems, for example formation of incompletely processed gene products, namely gene products having a preproleader-derived Glu-Ala sequence added (e.g. Japanese Patent Laid-open No. 132892/1984; Japanese Patent Laid-open No. 502661/1987), and generally low production efficiency and low productivity because of various processing steps, such as proteolysis and glycosylation steps, being rate-limiting steps.

DISCLOSURE OF THE INVENTION

Accordingly it is an object of the invention to provide a method of producing peptides or proteins which is generally applicable and enables large-scale treatment.

Another object of the invention is to provide a method of producing peptides or proteins which makes it possible to cause a wide range of host microorganisms to produce heterologous fusion proteins and then excise desired gene products efficiently from the fusion proteins using a highly specific enzyme.

A further object of the invention is to provide a method of producing peptides or proteins which comprises in vitro limited proteolysis of fusion proteins following their production.

The invention has been made based on the fact that many precursors containing a dipeptide, such as Lys-Lys, Arg-Lys, Lys-Arg or Arg-Arg, as a processing signal are processed into physiologically active peptides and mature proteins and that therefore these dipeptides are absent in physiologically active peptides and mature proteins in many instances. In accordance with the present invention, desired gene products are produced as fusion proteins using host microorganisms following insertion of a base sequence coding for a dipeptide which is a processing signal such as mentioned above between DNA fragments coding for a carrier and a desired gene product. It has been found that desired peptides or proteins can be obtained in the mature form from fusion proteins produced in the above manner when the latter are treated with a protease capable of specifically recognizing the dipeptide mentioned above and specifically hydrolyzing at the C terminus or N terminus of or between said dipeptide or an appropriate combination of such protease and an aminopeptidase capable of specifically liberating a basic amino acid residue from the N-terminal side or a carboxypeptidase capable of specifically liberating a basic amino acid residue from the C-terminal side. Thus the invention provides a method of producing peptides or proteins which comprises causing a host microorganism to produce a fusion protein of the formula 1a $$A\text{-}B\text{-}C \quad [Ia]$$

or $$C\text{-}B\text{-}A \quad [Ib]$$

wherein A stands for a carrier, B for an enzymatically cleavable dipeptide of the formula $X_1$–$X_2$ (in which $X_1$ is Lys, Arg or Pro bound to the C terminus of A and $X_2$ is Lys or Arg bound to the N terminus of C provided that when $X_1$ is Pro, $X_2$ is Arg), C for a desired peptide or protein, and then treating said fusion protein at least with a protease capable of specifically recognizing the dipeptide mentioned above and specifically hydrolyzing a peptide bond of said dipeptide.

The invention also provides a method of producing peptides or proteins which comprises causing a host microorganism to produce a fusion protein containing at least one unit of the formula $$\text{+B—C+}_n \quad [II]$$

or $$\text{+C—B+}_n \quad [III]$$

wherein B stands for an enzymatically clearable dipeptide of the formula $X_1$–$X_2$ (in which $X_1$ is Lys, Arg or Pro and $X_2$ is Lys or Arg provided that when $X_1$ is Pro, $X_2$ is Arg), C for a desired peptide or protein, and n for an integer of 2 or more, and then treating said fusion protein at least with a protease capable of specifically recognizing the dipeptide mentioned above and specifically hydrolyzing a peptide bond of said dipeptide.

The term "carrier" is used herein to include a spacer or peptide or the like which lies between A and B.

A typical example of the carrier is *Staphylococcus aureus*-derived protein A. The desired peptide or protein includes, among others, vasoactive intestinal polypeptide (VIP) precursors.

The protease may be used either alone or in combination with an aminopeptidase capable of specifically liberating a basic amino acid or acids alone from the N-terminal side of the peptide chain and/or a carboxypeptidase capable of liberating a basic amino acid or acids from the C-terminal side of the peptide chain as selected according to the structure of the fusion protein and the site of cleavage of the dipeptide by the protease.

The dipeptide-specific protease includes, among others, basic amino acid residue pair-specific proteases derived from yeasts, for example yeasts belonging to the genus Saccharomyces. The aminopeptidase is, for example aminopeptidase B (E.C. 3.4.11.6). The carboxypeptidase includes, among others, carboxypeptidase B (E.C. 3.4.17.2), carboxypeptidase E (enkephalin convertase), carboxypeptidase N (E.C. 3.4.17.3) and yscα.

The host microorganism includes microorganisms of the general Escherichia, Bacillus and Staphylococcus, among others.

The production of desired gene products by treating fusion proteins produced in heterologous hosts with a paired basic amino acid residues-specific protease has not yet been reported in the literature.

The present invention further includes, within the scope thereof, a method of producing peptides or proteins which combinedly utilizes an appropriate chemical modification, for example the reversible modification of Lys with citraconic anhydride.

In the present specification, peptides are described in the ordinary manner of sequence description, with the N-terminal side on the left side and the C-terminal side on the right.

The objects and advantages of the present invention will become more apparent from the following detailed description.

DESCRIPTION OF THE DRAWINGS

FIG. 2 shows a construction scheme for a plasmid named pMD321a.

FIG. 3 shows a construction scheme for a plasmid named pMD321R5a.

DETAILED DESCRIPTION OF THE INVENTION

Figure 1:
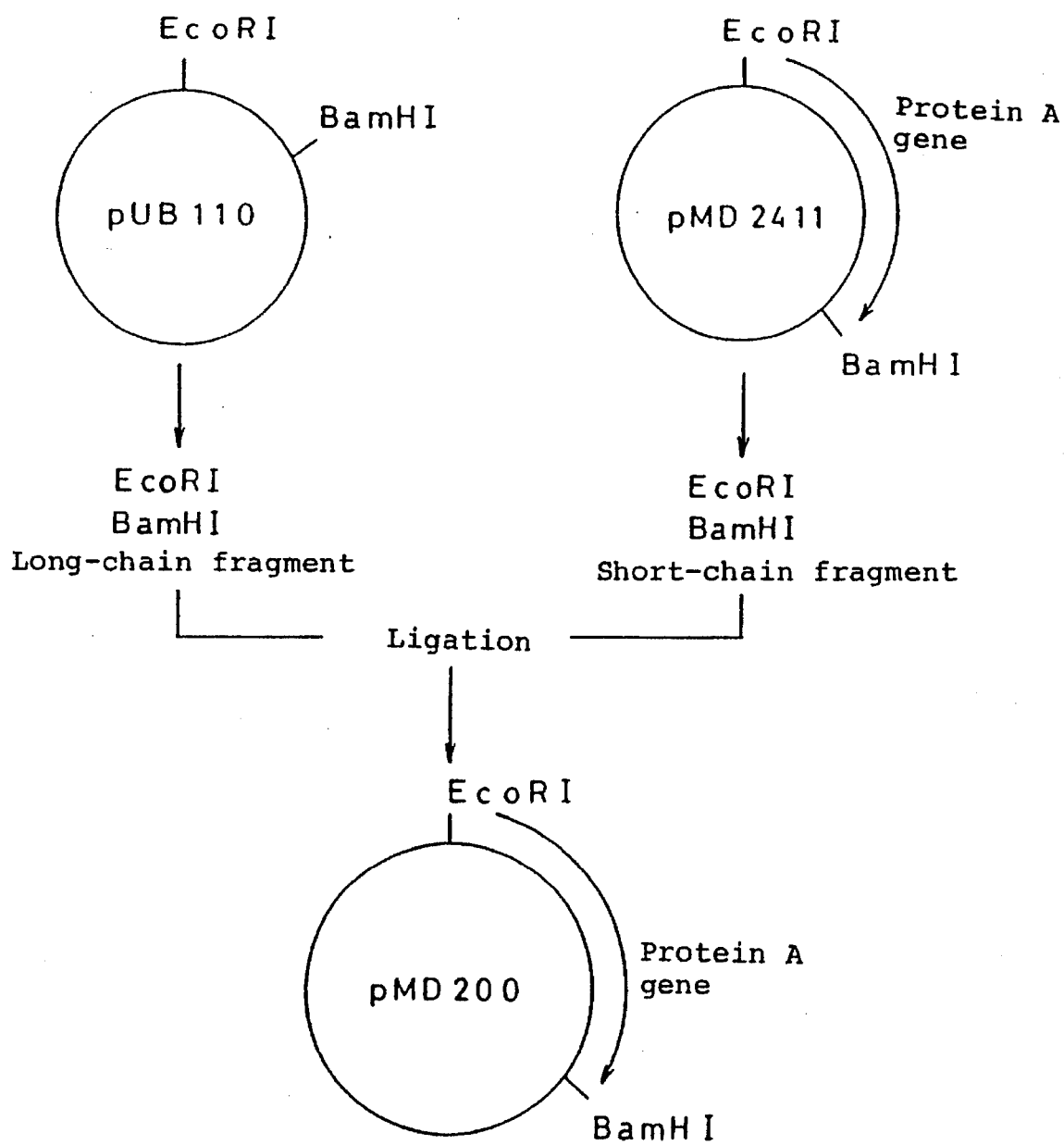
FIG. 1 shows a construction scheme for a plasmid named pMD200.

The carrier A may be of any kind provided that it is a peptide or protein produced by a host microorganism intracellularly or extracellularly or in the periplasm. Any dipeptide $X_1-X_2$ should preferably be absent in A, however. As such carrier A, there may be mentioned the whole or part of α-amylase, neutral or alkaline protease, cellulase, β-lactamase, β-galactosidase, chloramphenicol acetyltransferase, RecA protein, trpE, human interleukin-2, human growth hormone, dihydrofolate reductase, protein A, λcII, alkaline phosphatase, penicillinase or the like; and derivatives thereof. Said derivatives include, among others, derivatives resulting from deletion, substitution or addition of Cys and from deletion of an internal sequence such as the dipeptide $X_1-X_2$.

The carrier A may be an amino acid in certain instances. The carrier A may further be such that it gives a fusion protein resulting from joining of Met corresponding to the initiation codon alone directly or via one to scores of amino acids to the N terminus of the processing signal just before the desired gene product.

Preferred examples of the carrier include *Staphylococcus aureus*-derived protein A and the like. The gene for *Staphylococcus aureus* protein A contains a promoter participating in gene expression, a ribosome binding site, and a region coding for a secretion signal and for the protein.

The protease may be of any origin provided that it is a protease capable of specifically recognizing the dipeptide $X_1-X_2$, namely Lys-Lys, Arg-Lys, Lys-Arg, Arg-Arg or Pro-Arg and catalyzing specific hydrolysis at the C-terminal side or N-terminal side of or between the dipeptide.

As the protease catalyzing specific hydrolysis in the middle of Lys-Arg, Arg-Arg, Arg-Lys or Lys-Lys, there may be mentioned *Escherichia coli*-derived OmpT protease [protease VII; K. Sugimoto et al., J. Bacteriol., 170, 5625–5632 (1988)], *Salmonella typhimurium*-derived E protein [J. Grodberg and J. J. Dunn, J. Bacteriol., 171, 2903–2905 (1989)], and a protease involved in biosynthesis of analgesic peptides [W. Demmer and K. Brand, Biochem. Biophys. Res. Commun., 138, 356–362 (1986)], among others.

As the protease catalyzing specific hydrolysis at the N terminus of Arg-Lys or Arg-Arg, there may be mentioned, for example, a protease involved in maturation of somatostatin [P. Gluschankof et al., J. Biol. Chem., 262, 9615 to 9620 (1987)].

As the protease catalyzing specific hydrolysis at the C terminus of Lys-Arg or Arg-Arg, there may be mentioned, among others, IRCM-serine protease 1 [J. A. Cromlish et al., J. Biol. Chem., 261, 10850–10858 (1986)], POMC converting enzyme [Y. P. Loh et al., J. Biol. Chem., 260, 7194–7205 (1985)], a Saccharomyces-derived protease [K. Mizuno et al., Biochem. Biophys. Res. Commun., 144, 807–814 (1987)], proteases derived from Kluyveromyces, Sporobolomyces, Filobasidium, Hansenula, Issatchenkia, Pichia, Rhodosporidium, and Saccharomycopsis (Japanese Patent Laid-open Nos. 191683/1989 and 49585/1990).

Many physiologically active peptides or proteins in mature form are produced by hydrolytic processing at the C-terminal side of Lys-Arg or Arg-Arg. Therefore, proteases specifically recognizing Lys-Arg or Arg-Arg and catalyzing hydrolysis at the C-terminal side thereof are particularly preferred. A more preferred protease is a yeast-derived, paired basic amino acid residues-specific protease. This protease catalyzes specific hydrolysis at the C-terminal side of Lys-Arg and Arg-Arg (or Pro-Arg) but will not cleave the Arg-Lys or Lys-Lys sequence. Since it is of a yeast origin, it can be readily prepared in large quantities and generally shows high-level safety. For these and other reasons, it is particularly preferred.

The protease can be used solely when it specifically recognizes the dipeptide and specifically hydrolyzes the dipeptide at the C or N terminus to give a desired peptide or protein.

According to the structure of the fusion protein and the cleavage site of the dipeptide, the protease may be used in combination with an aminopeptidase releasing a basic amino acid from the N-terminal side and/or a carboxypeptidase releasing a basic amino acid from the C-terminal side.

The carboxypeptidase or aminopeptidase specifically recognizing a basic amino acid and releasing a basic amino acid from the C- or N-terminal side of the dipeptide, respectively, may be of any origin provided that it has the specificity mentioned above. Thus, as the carboxypeptidase and aminopeptidase, there may be mentioned, for example, carboxypeptidase B (E.C. 3.4.17.2), carboxypeptidase E (enkephalin convertase), carboxypeptidase N (E.C. 3.4.17.3), yscα [*Saccharomyces cerevisiae*-derived KEX1 gene product; A. Dmochowska et al., Cell, 50, 573–584 (1987)], and aminopeptidase B (E.C. 3.4.11.6).

The desired peptide or protein, C, is not limited to any particular species. Thus the peptide or protein, C, includes, among others, various physiologically active peptides, such as insulin, gastrin, various opioid peptides, epidermal growth factor, endothelin, VIP, atrial natriuretic peptide (ANP), substance P, calcitonin, insulin-like growth factors I and II, galanin, motilin and vasopressin, and precursors of these; inhibitors such as hirudin, eglin C and secretory leukocyte-derived protease inhibitor, human albumin, blood coagulation factors, various differentiation inducing factors and growth factors such as lymphokines, nerve growth factor and liver cell regeneration factor, and the like proteins, and precursors of these.

Among preferred peptides, there are VIP precursors. VIP is composed of 28 amino acid residues and has pharmacological activities such as vasodilating activity and blood flow increasing activity [Science, 169, 1217 (1970)]. VIP has the following amino acid sequence:

H—His—Ser—Asp—Ala—Val—Phe—Thr—Asp—Asn—Tyr—Thr—Arg—Leu—

Arg—Lys—Gln—Met—Ala—Val—Lys—Lys—Tyr—Leu—Asn—Ser—Ile—Leu—

Asn—NH$_2$ (SEQ ID NO: 1)

The VIP represented by this amino acid sequence differs from the VIP described in the prior art literatures [Japanese Patent Laid-open No. 296996/1989 and Eur. J. Biochem., 178, 343–350 (1988)] in that the 17th amino acid is not Leu but Met.

The VIP precursors mentioned above (hereinafter referred to as VIP-Gly) are derived from VIP by addition of Gly-X to the C terminus of VIP, as shown by the following amino acid sequence:

H—His—Ser—Asp—Ala—Val—Phe—Thr—Asp—Asn—Tyr—Thr—Arg—Leu—

Arg—Lys—Gln—Met—Ala—Val—Lys—Lys—Tyr—Leu—Asn—Ser—Ile—Leu—

Asn—Gly—X wherein X is OH (SEQ ID NO: 2), Lys-OH (SEQ ID NO: 3), Arg-OH (SEQ ID NO: 4), Lys-Arg-OH (SEQ ID NO: 5) or Arg-Lys-OH (SEQ ID NO: 6).

In one aspect of the invention, the fusion protein is composed of the carrier A mentioned above and the desired peptide or protein, C, joined together via the enzymatically cleavable spacer sequence B, namely the dipeptide $X_1$–$X_2$, as represented below by the formula [Ia] or [Ib], and should be producible in a host microorganism.

A-B-C [Ia]

C-B-A [Ib]

When the fusion protein has the structure A-B-C [Ia], said fusion protein is preferably treated with a protease recognizing B and specifically hydrolyzing the same at the C-terminal side and, when it has the structure C-B-A [Ib], with a protease recognizing B and specifically hydrolyzing the same at the N-terminal side, to give the desired peptide or protein.

It is also possible to obtain desired products by combinedly using an appropriate protease specifically recognizing a paired basic amino acid residues and hydrolyzing the peptide bonds on the N- or C-terminal side or between said pair thereof and an appropriate exopeptidase. For instance, it is possible to obtain desired products by treating fusion proteins having the structure A-B-C [Ia] with a combination of a protease recognizing B and specifically hydrolyzing the peptide bond on the N-terminal side or between the same thereof and an aminopeptidase specifically releasing only basic amino acids from the N-terminal side of the peptide. It is further possible to obtain desired products by treating fusion proteins having the structure C-B-A [Ib] with a protease recognizing B and specifically hydrolyzing the peptide bond on the C-terminal side or between the same thereof in combination with a carboxy-peptidase specifically releasing basic amino acids from the C-terminal side of the peptide.

Furthermore, in the case of desired gene products which are relatively low molecular weight peptides composed of less than 100 amino acids, for instance, attempts have been made to produce such products as tandem-type fusion proteins comprising a tandem repeats of desired peptides of the same kind as linked to a carrier so that the production and productivity can be increased. For obtaining desired gene products by the tandem-type fusion protein method, it is necessary to connect the desired peptides via an appropriate spacer and later completely eliminate the spacer from the fusion proteins. Concerning this tandem-type fusion protein method, it is reported that a Lys-free peptide (atrial natriuretic peptide, ANP) can be produced by producing a tandem-type fusion protein with Lys-Ser-Ser-Lys (SEQ ID NO: 23) as the spacer and thereafter treating said protein with lysyl endopeptidase and carboxypeptidase B to give the desired peptide [M. Lennick et al., Gene, 61, 103–112 (1987)]. However, such a method can be applied only to those desired peptides that contain no Lys residue, hence are lacking in general applicability. Several similar methods have been reported (e.g. Japanese Patent Laid-open Nos. 226998/1987 and 71195/1988) but these methods, like the method just mentioned above, have various problems; for example, they are lacking in general applicability, multiple reaction steps are required, and the spacer has a great length.

The method of the invention is very useful even in the production of desired peptides by such a tandem-form fusion protein method. Thus, mature peptides can be obtained efficiently in large quantities by producing a tandem-type fusion protein with the dipeptide B represented by $X_1$–$X_2$ inserted between each two units of the desired peptide and then treating said fusion protein with a combination of a dipeptide-specific protease, paired basic amino acid residues-specific aminopeptidase and a basic amino acid-specific carboxy-peptidase.

In special cases, namely when the C-terminal amino acid of the desired peptide or protein is Pro, insertion of Arg as a spacer can result in efficient hydrolysis of the peptide bond on the C-terminal side of the Pro-Arg sequence by paired basic amino acid residues-specific protease derived from a yeast such as *Kluyveromyces lactis* or *Sporobolomyces odorus*. Utilizing this fact, it is possible to obtain desired peptides or proteins by specifically hydrolyzing the peptide bond on the C-terminal side of Pro-Arg with the above protease, followed by treatment with prolin carboxypeptidase (E.C. 3.4.16.2).

The tandem-form fusion protein should meet the only requirements that it contains at least one unit of the formula [II] or [III] given below and that it can be produced in a host microorganism. The carrier A may be absent in the tandem-form fusion protein if the latter can be produced in a microorganism.

$$(B-C)_n \quad [II]$$

$$(C-B)_n \quad [III]$$

In the above formulas, B stands for an enzymatically cleavable dipeptide of the formula $X_1-X_2$ (in which $X_1$ is Lys, Arg or Pro and $X_2$ is Lys or Arg provided that when $X_1$ is Pro, $X_2$ is Arg), C for a desired peptide or protein, and n for an integer of 2 or more.

It is to be understood that when, in the above formula [II] or [III], the N terminus or C terminus has no carrier A, dipeptide B or desired peptide C bound thereto, an amino acid H atom is bound to the N terminus or an amino acid OH group to the C terminus, respectively.

The tandem-form fusion protein containing the above-mentioned unit [II] may have any of the following structures:

$$A(B-C)_n \quad [IIa]$$

$$C(B-C)_n B-A \quad [IIb]$$

$$C(B-C)_n A \quad [IIc]$$

$$C(B-C)_n \quad [IId]$$

and the like. The tandem-form fusion protein containing the above unit [III] may have any of the following structures:

$$(C-B)_n A \quad [IIIa]$$

$$A-B(C-B)_n C \quad [IIIb]$$

$$A(C-B)_n C \quad [IIIc]$$

$$(C-B)_n X \quad [IIId]$$

and the like.

Preferred among the above-mentioned structures given for the tandem-form fusion protein are the structures [IIa], [IIb], [IIIa] and [IIIb] in which the carrier A is bound to the dipeptide B and the structures [IIc] and [IIIc] in which the carrier A is bound to a tandem structure comprising the desired peptide C and the dipeptide B. Particularly preferred are the structures [IIa], [IIb] and [IIc].

The desired peptide or protein can be obtained from the tandem-form fusion protein by treating the latter with a protease specifically recognizing B and specifically hydrolyzing the peptide bond of the dipeptide and, as necessary, simultaneously or sequentially with an endopeptidase specifically releasing a basic amino acid from the C-terminal or N-terminal side of the peptide chain as selected according to the mode of binding of the fusion protein. More specifically, the desired peptide or protein can be obtained by treating the tandem-form fusion protein with a protease specifically recognizing B and specifically hydrolyzing the peptide bond on the C-terminal side of said dipeptide and a carboxypeptidase specifically releasing a basic amino acid from the C-terminal side of the peptide chain, either simultaneously or sequentially. Similarly the desired peptide or protein can be obtained by treating said fusion protein with a protease specifically recognizing B and specifically hydrolyzing the peptide bond on the N-terminal side of the dipeptide and an aminopeptidase specifically releasing a basic amino acid from the N-terminal side of the peptide chain, either simultaneously or sequentially. Furthermore, the desired peptide or protein can also be obtained by treating said fusion protein with a protease specifically recognizing B and specifically hydrolyzing the peptide bond between the same, an aminopeptidase specifically releasing a basic amino acid from the N-terminal side of the peptide chain and a carboxypeptidase specifically releasing a basic amino acid from the C-terminal side of the peptide chain, either simultaneously or sequentially.

In a particularly preferred embodiment, a tandem-form fusion protein containing the sequence Lys-Arg or Arg-Arg inserted between each two units of the desired peptide is produced and this fusion protein is then treated with a protease specifically recognizing Lys-Arg or Arg-Arg and hydrolyzing the peptide on the C-terminal side of the dipeptide and a basic amino acid-specific carboxypeptidase to give the desired peptide. This embodiment has a number of advantages, for example in that the sequence to be inserted between the desired peptide units is very short and contains only two amino acids, that the content of the insert dipeptide $X_1-X_2$ in the peptide is very low and therefore the general applicability is very high, and that two or three enzymes can be used simultaneously, hence the procedure is easy and simple and involves a smaller number of steps.

In cases where Lys or Arg is present on the N-terminal or C-terminal side of the desired peptide or protein, that structure should be fully utilized in designing the structure of the fusion protein, and the method of cleavage should be selected according to the structure of the desired peptide or protein. More detailedly, for some C-terminally amidated peptides, it is reported that the corresponding biosynthetic precursor peptides having a C-terminal extension of Gly-Lys-Arg are more active than the mature peptides (Japanese Patent Laid-open No. 246595/1987). For producing such peptides, tandem-form fusion proteins resulting from insertion of Gly-Lys-Arg as a spacer between every two peptide units are produced and then they are treated with a protease specifically recognizing Lys-Arg and specifically hydrolyzing the peptide bond on the C-terminal side of the same, whereby the desired peptides having an extension of Gly-Lys-Arg can be obtained. Similarly, it is possible to obtain peptides having a extension of Gly-Lys by treating the above-mentioned fusion proteins with a protease specifically recognizing Lys-Arg and specifically hydrolyzing the peptide bond between the same thereof and an aminopeptidase specifically releasing a basic amino acid from the N-terminal side, either simultaneously or sequentially. Similar peptides having an extension of Gly-Lys can be obtained by treating the above fusion proteins with a protease specifically recognizing Lys-Arg and hydrolyzing the peptide bond on the C-terminal side of the same thereof and a carboxypeptidase specifically releasing Arg alone from the C-terminal side, either simultaneously or sequentially.

The advantageous feature of the production method of the present invention is now explained in more detail taking the above-mentioned VIP-Gly as an example. Since VIP-Gly internally contains possible processing signals such as Met, Arg, Arg-Lys, Lys-Lys and Asp, as mentioned above, the conventional methods so far reported can hardly excise VIP-Gly from fusion proteins. However, a yeast-derived, paired basic amino acid residues-specific protease is characteristically capable of specifically recognizing the sequence X-Arg (X being Lys, Arg or Pro) and preferentially hydrolyzing the peptide bond on the C-terminal side of this dipeptide thereof. When this fact is utilized, the production of VIP-Gly becomes possible. Thus, for example, using a carrier composed of a segment of protein A (positions 1 through 402) and Arg-Gly-Ser-Ser-Arg-Val-Asp-Val-Ile-Glu-Gly-Arg-Met-Thr-Ile-Phe-Thr-Phe-Arg (SEQ ID NO: 7), which is a spacer, linked together, and using, as the desired peptide, a peptide composed of five molecules of VIP-Gly (SEQ ID NO: 2) linked to each other via Lys-Arg, a tandem-form fusion protein [hereinafter abbreviated as PAVIPG(P)R5] resulting from said carrier and said peptide is produced extracellularly in an secretory manner using *Bacillus subtilis* as a host. Said PAVIPG(P)R5 contains Ile-Glu-Gly-Arg (SEQ ID NO: 20), which is a recognition sequence for blood coagulation factor Xa, Phe-Arg, which is a recognition sequence for kallikrein, and Lys-Arg, which is a recognition sequence for a *Kluyveromyces lactis*-derived, paired basic amino acid residues-specific protease. After purification, PA-VIPG(P)R5 is subjected to partial digestion with a *Kluyveromyces lactis*-derived, paired basic amino acid residues-specific protease (Japanese Patent Laid-open No. 49585/1990; hereinafter abbreviated as PBRS-protease) alone, whereby cleavage occurs at the C-terminal peptide bond of Lys-Arg to give VIP-Gly-Lys-Arg (SEQ ID NO: 5) and VIP-Gly (SEQ ID NO: 2). Furthermore, VIP-Gly (SEQ ID NO: 2) can be obtained singly by treating PAVIPG(P)R5 with PBRS-protease and a carboxypeptidase, either simultaneously or sequentially.

The host microorganism to be employed for producing the above-mentioned fusion proteins preferably belongs to the genus Escherichia, Bacillus or Staphylococcus, although it may be a yeast or a fungus. Microorganisms of the genus Bacillus, in particular *Bacillus subtilis*, are highly safe and extracellularly secrete proteins in large quantities. Preferred among strains of *Bacillus subtilis* are those strains that show a decreased extracellular protease production as a result of application of such a technique as mutagenesis. By transforming such strains with an appropriate plasmid, the degradation of fusion proteins by host-derived protease can be inhibited to a significant extent and, as a result, VIP-Gly can be obtained efficiently in large quantities.

As strains of *Bacillus subtilis* which show low protease productivity, there may be mentioned, for example, (1) *Bacillus subtilis* DB104 [J. Bacteriol., 160, 442–444 (1984)] and *Bacillus subtilis* 104HL [Biochem. Biophys. Res. Commun., 128, 601–606 (1985)]; (2) *Bacillus subtilis* DY-16 (deposited with the Fermentation Research Institute, Agency of Industrial Science and Technology under the deposit number FERM P-9488) proposed by the present applicant in Japanese Patent Laid-open No. 37284/1989; and (3) mutant strains derived from *Bacillus subtilis* strains lacking in ability to produce either alkaline protease or neutral protease and showing a protease activity of not more than 3% as compared with wild strains by introduction of the spoOAΔ 677 mutant gene. Particularly preferred are strains belonging to the above-mentioned category (3), and such strains include, among others, *Bacillus subtilis* SPO11 (deposited as deposit number FERM BP-5050, at the National Institute of Bioscience and Human-Technology, Agency for Industrial Science and Technology, 1–3, Higashi 1 chome, Tsukuba-shi, Ibaraki-ken 305, Japan) derived from *Bacillus subtilis* 104HL by introduction of the spoOAΔ677 mutant gene, as proposed by the present inventors in Japanese Patent Application No. 281440/1989, and *Bacillus subtilis* SPL14 (deposited as deposit number FERM BP-5051, at the National Institute of Bioscience and Human-Technology, Agency for Industrial Science and Technology, 1–3, Higashi 1 chome, Tsukuba-shi, Ibaraki-ken 305, Japan) derived from *Bacillus subtilis* DY-16 by introduction of the spoOAΔ677 mutant gene.

Treatment of fusion proteins with protease may be performed under conditions adapted to the protease employed, namely in an appropriate buffer at an appropriate pH in the presence of an appropriate additive or additives. As said additives, there may be mentioned, for example, urea, guanidine hydrochloride, calcium chloride; ionic, nonionic or amphoteric surfactants such as sodium lauryl sulfate (hereinafter abbreviated as SDS), Triton X-100 and Lubrol PX; organic solvents such as methanol, ethanol, isopropanol and acetonitrile; inhibitors such as diisopropyl fluorophosphate (DFP), phenylmethanesulfonyl fluoride (PMSF), parachloromercuriobenzoic acid (PCMB), iodoacetamide (IAA), ethylenediaminetetraacetate (EDTA), o-phenanthroline, leupeptin and pepstatin A; and so on. More concretely, when the *Kluyveromyces lactis*-derived, basic amino acid residue pair-specific PBRS-protease is used, the reaction conditions may be as follows: pH 6 to 10, preferably about 6 to 8, temperature 15° to 60° C., preferably about 25° to 50° C. The additive concentrations may suitably be selected; for example, the concentration of calcium chloride is preferably about 0.01 to 10 mM, the concentration of urea is preferably about 0.1 to 6M, the concentration of SDS is about 0.001 to 0.1%, and the concentration of Lubrol PX is preferably about 0.01 to 10%. The pH may be adjusted by addition of an appropriate acid or base or with an appropriate buffer, for example a buffer containing Tris hydrochloride, phosphoric acid, succinic acid, acetic acid, 3,3-dimethylglutaric acid, or fumaric acid.

The enzyme should preferably be highly pure. The purity is not critical, however, if hydrolysis will not occur at sites other than the desired site of the substrate fusion protein. The reaction may also be conducted using a low-purity enzyme in the presence of an inhibitor. In that case, when the inhibitor is one that will not inhibit the protease employed but inhibits contaminant proteases causing hydrolysis at sites other than the desired site, it is also possible to prevent protease-caused degradation at other sites than the desired site.

For partial digestion of each micromole of the substrate fusion protein, the enzyme protease is used in an amount of 0.001 to 100 U, preferably about 0.01 to 10 U. One unit (1 U) corresponds to an amount of enzyme which hydrolyzes one micromole of a low-molecular synthetic substrate, for example Boc-Gln-Arg-Arg-MCA (Boc=t-butoxycarbonyl; MCA=4-methylcoumaryl- 7-amide), per minute at the desired site (between Arg-Arg and MCA). When an aminopeptidase and/or a carboxypeptidase is used separately or simultaneously with the protease, the aminopeptidase and/or carboxy-peptidase is used each in an amount of about 0.01 to 10,000 times, preferably about 10 to 1,000 times, the amount of the endopeptidase-type protease.

The reaction between substrate fusion protein and enzyme may be carried out batchwise using a free enzyme or an enzyme immobilized on a carrier. The carrier for the immobilized enzyme includes conventional carriers such as polyacrylamide, chitin, dextran, kappa carrageenan, celite, and cellulose. The reaction may also be conducted using a free enzyme in combination with a membrane-type bioreactor, or using a continuous type bioreactor together with an immobilized enzyme.

The host microorganism to be used for the production of a fusion protein such as mentioned above can be prepared using conventional gene manipulation techniques. For example, when the host microorganism is to produce a fusion protein linked to a carrier, A, it can be prepared as follows.

First, corresponding to the structure of the fusion protein mentioned above, a gene coding for a carrier A is jointed to a gene coding for a peptide or protein, C, via a gene coding for a dipeptide B such as mentioned above. To the resultant gene fragment are joined a promoter, which is a control site for expression, a ribosome-binding site and, as necessary, a secretion signal. A plasmid can be constructed by ligating the thus-obtained DNA fragment to a vector DNA. For the construction, conventional DNA ligation techniques, such as the restriction enzyme method comprising ligating the DNA and vector DNA, each cleaved with a restriction enzyme or enzymes, to each other using a ligase and the linker method, can be used.

The vector DNA may be any DNA capable of replicating in a host microorganism. A plasmid DNA capable of replicating in at least one of the Bacillus strains mentioned above is preferred, however. As such vector, there may be mentioned, for instance, the Staphylococcus-derived plasmids pUB110, pC194, pBD64, pE194, pSA0501 and pT127, and derivatives of these. A preferred vector DNA is the DNA of the plasmid pUB110. *Bacillus subtilis* strains containing these plasmids are available from the Ohio University Bacillus Stock Center (address: 484, West 12th Avenue, Columbus, Ohio, 43210 U.S.A.).

In the case of the production of tandem-form fusion proteins, conventional gene manipulation techniques can be utilized for constructing a gene coding for a plurality of peptide and for ligating gene fragments. In that case, a vector whose host is *Escherichia coli*, for instance, can also be used. When VIP-Gly is taken as an example, the construction of a tandem-form gene may be explained as follows. For constructing a gene coding for a plurality of VIP-Gly molecules, the fact that the base sequence GACNNNGTC, which is a recognition and cleavages sequence for the restriction enzyme Tth111I, is present on the 5' side of the VIP-Gly gene can be used. The fragment resulting from cleavage with said restriction enzyme Tth111I, has cohesive ends that have no symmetric structure. Therefore the site of cleavage by the restriction enzyme Tth111I can be utilized as a very useful cleavage site for introducing a plurality of genes coding for the peptide in the desired direction. Thus, as the VIP-Gly gene to be inserted, a gene is synthesized which has a cleavage site for the restriction enzyme Tth111I on the 5' side and has no cleavage site for said restriction enzyme on the 3' side. Separately, a plasmid with one VIP-Gly gene introduced therein is cleaved with the restriction enzyme Tth111I, and the phosphate residue on the 5' side is removed using alkaline phosphatase. The above-mentioned VIP-Gly gene insert is ligated to the cleaved plasmid using a DNA ligase. *Escherichia coli* is transformed with the vector obtained, and the transformant is cultured for preparing the plasmid with two VIP-Gly genes introduced therein. Theoretically, the above procedure can be repeated as many times as desired utilizing said Tth111I cleavage site to arrange the VIP-Gly gene repeatedly in tandem. A plasmid in which a plurality of VIP-Gly genes are linked can be thus prepared.

Addition of a cleavage site recognizable by the restriction enzyme Tth111I to the 5' side of a gene coding for a peptide other than VIP-Gly, followed by successive ligation in the same manner as above can give a tandem arrangement of said other peptide-encoding gene.

The number of the above-mentioned peptide-encoding genes may be at least 2 but, generally, it is about 2 to 20.

The gene coding for a plurality of peptides may be extracted from a biological material or chemically synthesized. The gene coding for a plurality of peptides is preferably constructed using a plurality of chemically synthesized genes. Said plurality of peptides may be of the same kind or differ in kind.

Transformation of a host microorganism with the plasmid obtained in the above manner gives fusion protein-producing microorganism. The transformation of the host microorganism with said plasmid can be performed using conventional methods, for example the protoplast method of Chang et al., [Chang, S. et al., Mol Gen. Genet., 168, 111–115 (1979)].

The fusion protein mentioned above is obtained by cultivating a host microorganism transformed in the above manner. When the fusion protein is accumulated in cells or in the periplasm, the fusion protein can be recovered in the conventional manner, for example by disrupting cells. The host microorganism can be cultivated in the manner of conventional liquid culture. Thus, the transformant can be cultivated in a liquid medium containing conventional components, for example inorganic salts, carbon sources, nitrogen sources, growth factor components, etc., in the manner of shaking culture or aeration agitation culture. The pH of the medium is, for example, about 7 to 8. The cultivation can be conducted under conditions ordinary employed in cultivating microorganisms, for example at a temperature of 15° to 45° C., preferably 25° to 40° C., for about 6 to 60 hours.

INDUSTRIAL APPLICABILITY

The production method of this invention is useful in producing peptides and proteins which are useful as drugs, among others.

The following examples are further illustrative of the present invention but are by no means limitative of the scope of the invention. All enzymes used in the examples were purchased from Takara Shuzo Co. and the reactions were carried out under conditions recommended in the brochures provided by Takara Shuzo Co.

EXAMPLES

Example 1

Excision of VIP-Gly-Lys-Arg (SEQ ID NO: 5) and VIP-Gly (SEQ ID NO: 2) from the fusion protein PAVIPG(P)R5
(1) Preparation of a protease specific to basic amino acid residue pairs

*Kluyveromyces lactis* (IFO 1903) was cultivated in 30 liters of YM medium for 2 days. Cells weighing 314 g in the wet state were recovered by centrifugation, suspended in 300 ml of buffer 1 [10 mM Trishydrochloride buffer (pH 7.0), 0.5 mM calcium chloride] and disrupted in Dyno-Mill. The cell debris was removed by centrifugation (1,700 g, 10 minutes) and the supernatant obtained was subjected to ultracentrifugation (150,000 g, 60 minutes), whereby 79.4 g of a membrane fraction was prepared as a sediment. This membrane fraction was suspended in 600 ml of extraction buffer [10 mM Tris-hydrochloride buffer (pH 7.0), 3% Lubrol PX, 0.1M sodium chloride], and the suspension was stirred overnight for enzyme extraction and then subjected to ultracentrifugation to give a membrane extract as the supernatant.

This extract was heat-treated at 50° C. for 30 minutes, the resultant precipitate was removed by centrifugation (39,000 g, 20 minutes), and the supernatant was concentrated by ultrafiltration and then dialyzed against buffer 2 [10 mM Tris-hydrochloride buffer (pH 7.0), 0.5 mM calcium chloride, 0.2% Lubrol PX] to give a heat-treated membrane extract fraction.

This faction was applied to a DEAE-Toyopearl 650M column (2.5×40 cm) equilibrated, in advance, with buffer 2. The column was washed well with the same buffer and then enzyme was eluted by the sodium chloride gradient method (0 to 0.6M) to give an active fraction.

The active fraction was concentrated by ultrafiltration and then applied to a concanavalin A (Con A) Sepharose column (1.6×25 cm) equilibrated, in advance, with buffer 2 containing 0.5M sodium chloride. The column was washed well with the same buffer and elution was carried out using buffer 2 containing 0.5M sodium chloride and 0.67 M α-methyl D-mannoside. The active fraction obtained was concentrated to give a Con A-Sepharose fraction.

The Con A-Sepharose fraction was dialyzed against buffer 2 and then applied to an arginine-Sepharose column (1.6×50 cm) equilibrated, in advance, with the same buffer. After sufficient equilibration was attained, elution was carried out by the sodium chloride gradient method (0 to 0.5M). The active fraction obtained was concentrated by utrafiltration to give an arginine-Sepharose fraction.

The arginine-Sepharose fraction was dialyzed against buffer 2 and then applied to a Mono Q column (0.5×5.0 cm) equilibrated, in advance, with the same buffer. The column was washed well with the same buffer and then elution was carried out by the sodium chloride gradient method (0 to 0.5M), whereby two peaks were obtained as active fractions. These fractions were separately recovered and concentrated to give fractions designated as Mono Q-I and Nono Q-II. These fractions were individually dialyzed against buffer 2 and each applied to a benzamidine-Sepharose column (1.6× 5.0 cm) equilibrated, in advance, with the same buffer. The column was washed well with the same buffer and enzyme elution was carried out by the sodium chloride gradient method (0 to 0.5M). The active fractions obtained were designated as Benz-I and Benz-II fractions, respectively.

The process for purifying the basic amino acid residue pair-specific protease is summarized in the table given below.

TABLE 1

| Step | Volume (ml) | Protein (mg) | Activity (mU) | Specific activity (mU/mg) | Yield (%) | Purification factor (time) |
|---|---|---|---|---|---|---|
| Membrane Extraction | 1450 | 15000 | 52.4 | 0.00350 | | 1 |
| Heat treatment | 537 | 11000 | 989 | 0.0896 | 100 | 26 |
| DEAE-Toyopearl | 20.7 | 467 | 800 | 1.71 | 81 | 489 |
| Con A-Sepharose | 33.0 | 24.3 | 657 | 27.0 | 66 | 7730 |
| Arg-Sepharose | 17.1 | 12.8 | 326 | 25.4 | 33 | 7260 |
| Mono Q-I | 1.5 | 1.52 | 84.5 | 55.5 | 8.5 | 15900 |
| Benz-Sepharose I | 0.42 | 0.377 | 37.3 | 98.8 | 3.8 | 28200 |
| Mono Q-II | 2.1 | 2.90 | 73.6 | 25.4 | 7.4 | 7260 |
| Benz-Sepharose II | 0.55 | 0.431 | 25.2 | 58.4 | 2.5 | 16700 |

One unit (1 U) is defined as the activity liberating 1 micromole of AMC per minute when the enzyme acts on 0.1 mM Boc-Gln-Arg-Arg-MCA in 50 mM Tris hydrochloride buffer (pH 7.0) containing 1% Lubrol PX and 0.5 mM CaCl$_2$ at 30° C. (Boc stands for t-butoxycarbonyl, MCA for 4-methylcoumaryl-7-amide, and AMC for 7-amino-4-methylcoumarine.)

(2) Construction of the plasmid pMD200

A construction scheme is shown in FIG. 1 for the plasmid pMD200 capable of expressing the protein A gene of *Staphylococcus aureus* in *Bacillus subtilis*, which serves as a host, and allowing secretory production of protein A in the culture supernatant.

The plasmid pDCP2411 containing the protein A gene (cf. Japanese Patent Laid-Open No. 245677/1988) is a plasmid obtained by inserting the protein A gene cloned from a strain of *Staphylococcus aureus* into the plasmid pUC118 capable of replicating in *Escherichia coli*. The method of preparing pDCP2411 and the whole base sequence of the protein A gene contained in pDCP2411 are described in detail in the above-cited Japanese Patent Laid-open No. 245677/1988. pDCP2411 was prepared from an *Escherichia coli* transformant containing this plasmid by the alkaline lysis method [Sambrook et al., Molecular Cloning, 1.33 (1989)].

pDCP2411 was cleaved with the restriction enzymes EcoRI and BamHI and the resultant protein A gene-containing DNA fragment (about 1.9 kb; hereinafter referred to as protein A gene fragment) was separated by agarose gel electrophoresis and eluted and purified by the electroelution method [Sambrook et al., Molecular Cloning, 6.28 (1989)]. The above-mentioned protein A gene fragment contains the protein A gene promoter, ribosome-binding site, signal sequence for secretion and structural gene for protein A.

Then, pUB11.0 to serve as a vector was cleaved with the restriction enzymes EcoRI and BamHI, and a DNA fragment of about 3.7 kb (hereinafter referred to as pUB110 vector gene fragment) was separated in the same manner as above by agarose gel electrophoresis and eluted and purified by the electroelution method.

The protein A gene fragment was ligated to the pUB110 vector gene fragment using T4 DNA ligase. The plasmid pMD200 was thus constructed.

(3) Construction of a plasmid containing a gene coding for VIP

For constructing a VIP gene, the following eight genes were produced on a model ABI430A DNA synthesizer according to the amino acid sequence of VIP and the frequencies of use of the respective codons in *Bacillus subtilis*.

5'-TCTAGAGTCGACGTCATTGAAGGAAGAATG
ACAATTTTTACATTCAGGCATAGCGACG-3'   (SEQ ID No. 8)

3'-CTCAGCTGCAGTAACTTCCTTCTTAC
TGTTAAAAATGTAAGTCCGTATCGCTGCG-5'   (SEQ ID NO. 9)

5'-CAGTCTTCACAGATAACTACACGCGTTTAA
GAAAGCAAATGGCTGTG-3'   (SEQ ID NO: 10)

3'-TCAGAAGTCTCTATTGATGTGCGCAAATT
CTTTCGTTTACC-5'   (SEQ ID NO: 11)

5'-AAAAAATATTTGAATTCTATTCTTA
ACGGCTAATAGATCTAAAAAGAAGCAGG-3'   (SEQ ID NO: 12)

3'-GACACTTTTTTATAAACTTAAGATAAGAAT
TGCCGATTATCTAGATTTTTCTT-5'   (SEQ ID NO: 13)

5'-TTCCTCCATACCTGCTTCTTTTTAT
TTGTCAGCATCCTGATGTTGGATCCGCATG-3'   (SEQ ID NO: 14)

3'-CGTCCAAGGAGGTATGGACGAAGAAAAATA
AACAGTCGTAGGACTACAACCTAGGC-5'   (SEQ ID NO: 15)

Figure 2:
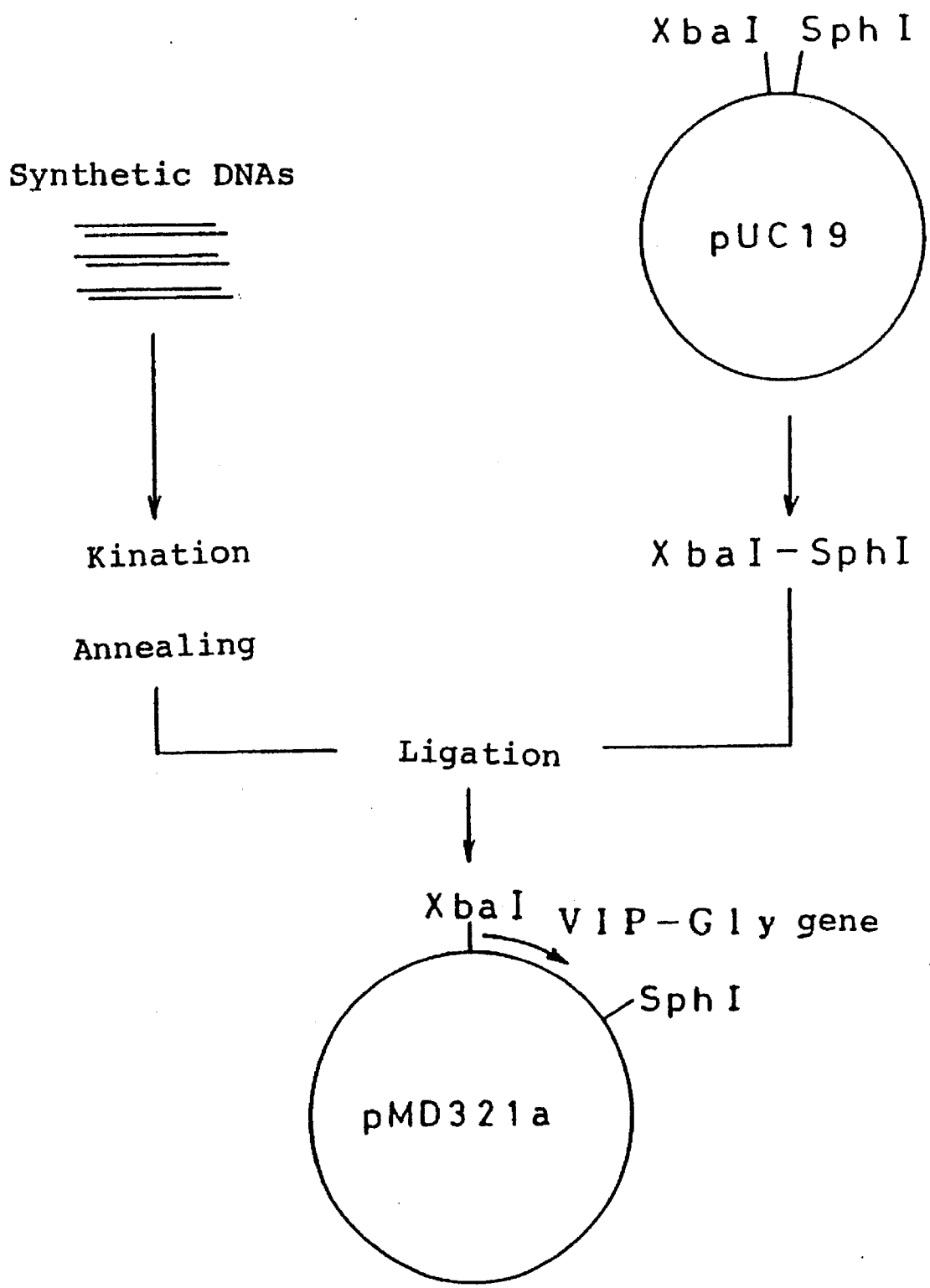

The 5' end of each synthetic DNA was phosphorylated using T4 DNA kinase. Separately, the plasmid pUC19 was cleaved with the restriction enzyme XbaI and SphI. The 5'-phosphorylated synthetic DNAs were inserted into pUC19 between the XbaI-SphI cleavage site using DNA ligase, whereby the plasmid pMD321a containing the VIP-Gly gene was constructed. The construction scheme for the plasmid pMD321a is shown in FIG. 2.

The base sequence of the synthetic gene segment in the thus-obtained pMD321a and the corresponding amino acid sequence are shown below.

```
EcoRI  SacI    KpnI   SmaIBamHI   XbaI
AATTCGAGCTCGGTACCCGGGGATCCTCTAGA
  Phe Glu Leu Gly Thr Arg Gly Ser Ser Arg

HicIIAatII                                60
GTCGACGTCATTGAAGGAAGAATGACAA
 Val Asp Val Ile Glu Gly Arg Met Thr Ile
                     Xa

Tth111I
TTTTTACATTCAGGCATAGCGACGCAGTCTTC
 Phe Thr Phe Arg His Ser Asp Ala Val Phe
       protein C ———> VIP 120
ACAGATAACTACACGCGTTTAAGAAAGC
 Thr Asp Asn Tyr Thr Arg Leu Arg Lys Gln EcoRI
AAATGGCTGTGAAAAAATATTTGAATTCTATT
 Met Ala Val Lys Lys Tyr Leu Asn Ser Ile BglII             180
CTTAACGGCTAATAGATCTAAAAAGAAG
 Leu Asn Gly★★★★★★

CAGGTTCCTCCATACCTGCTTCTTTTTATTTG
                   BamHI  SphI
                              240
TCAGCATCCTGATGTTGGATCCGCATGC

HindIII ┌───> pUC19 sequence
         │
AAGCTTGGCACTGGCCGTCGTTTACAACGTC

300
GTGACTGGGAAAACCCTGGCGTTACCCA
                   (SEQ ID NO: 16)
```

This synthetic gene segment is composed of a VIP-Gly-encoding base sequence, a gene occurring before said base sequence and coding for the sequence IleGluGlyArg (SEQ ID NO: 20), which is recognizable by the blood coagulation factor Xa, and genes coding for Met, which is cleavable with BrCN, and the sequence ThrIlePheThrPheArg (SEQ ID NO: 25), which is recognizable by protein C.

Downstream from the VIP-Gly gene, there is the *Bacillus subtilis* subtilisin terminator [M. Honjo et al., J. Biotechnology, 2, 75–85 (1985)] behind two termination codons (TAATAG).

(4) Construction of a plasmid containing a gene coding for 5 molecules of VIP

Figure 3:
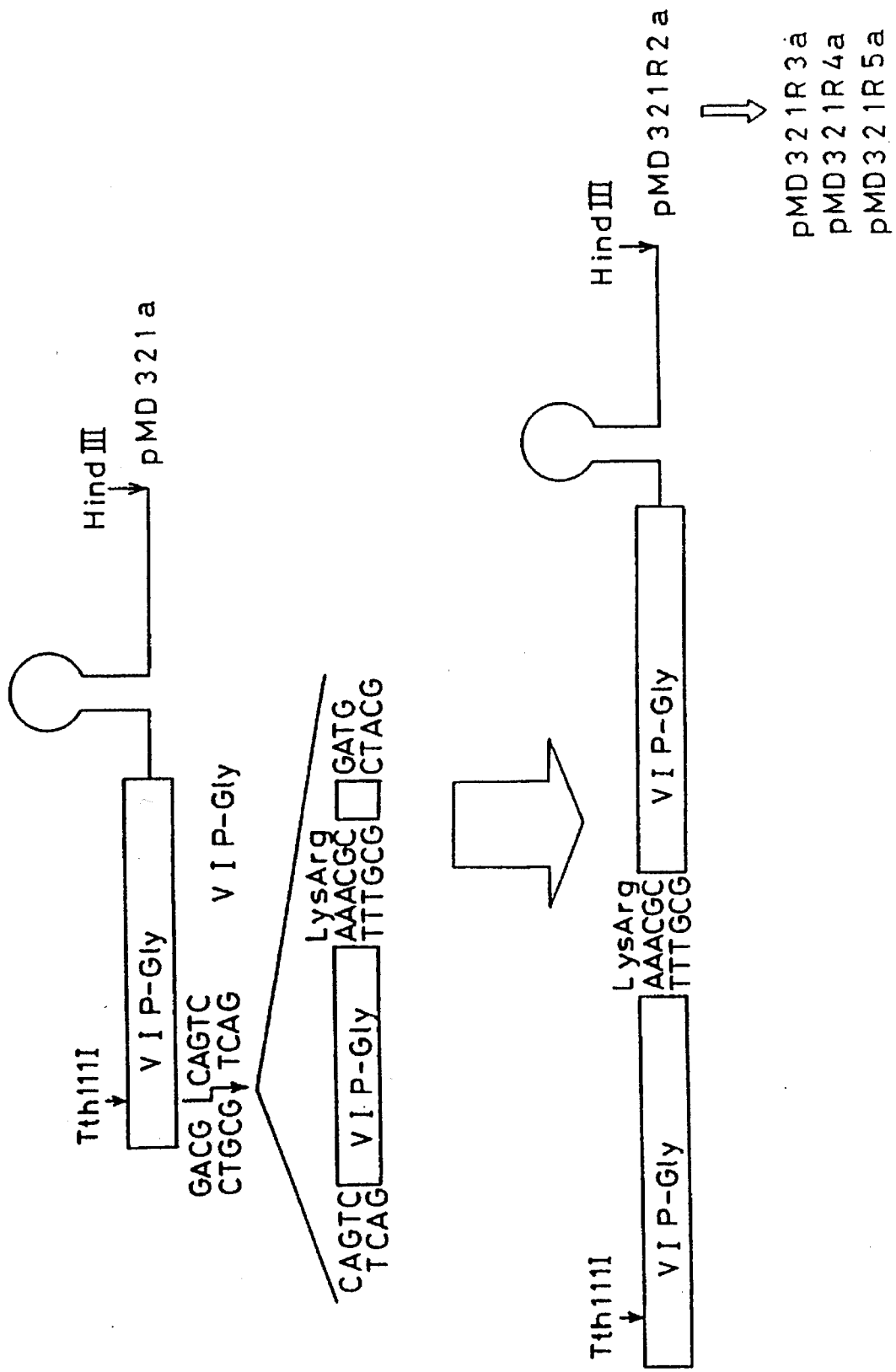

A construction scheme for the plasmid pMD321R5a containing a gene coding for 5 molecules of VIP (hereinafter referred to as tandem-form VIP gene) is shown in FIG. 3.

The VIP-Gly gene of pMD321a has, on the 5' side thereof, the base sequence GACGCAGTC which is a cleavage recognition sequence for the restriction enzyme Tth111I. On the other hand, as shown in FIG. 3, a gene retaining a Tth111I cleavage site on the 5' side of the VIP gene and incapable of being cleaved on the 3' side was synthesized.

Further, for recovering VIP-Gly molecules occurring in tandem by cleavage, a gene corresponding to Lys-Arg, which is a recognition sequence for cleavage by a basic residue pair-specific protease (Japanese Patent Laid-open No. 49585/1990), was introduced to thereby synthesize a VIP-Gly-Lys-Arg (SEQ ID NO: 5) gene for tandem arrangement, as shown in FIG. 3.

Then, pMD321a was completely cleaved with Tth111I, and the 5' side phosphate group was removed using alkaline phosphatase. The resultant fragment was admixed with the VIP-Gly-Lys-Arg (SEQ ID NO: 5) gene prepared for tandem arrangement, ligation was performed using DNA ligase, and the ligation mixture was used to transformation of *Escherichia coli* JM109.

Plasmid gene preparation from an ampicillin-resistant transformant thus obtained gave a plasmid, pMD321R2a, containing two VIP-Gly genes linked in tandem, as desired.

The thus-obtained pMD321R2a has a single cleavage site for Tth111I in the vicinity of the 5' region of the two tandem linked VIP-Gly genes.

pMD321R2a was cleaved with Tth111I and the 5' region thereof was dephosphorylated using alkaline phosphatase. The resultant fragment was mixed with the VIP-Gly-Lys-Arg gene for tandem arrangement and subjected to ligation using DNA ligase. *Escherichia coli* JM109 was transformed using the ligation mixture. Plasmid preparation from an ampicillin-resistant transformant thus obtained gave a plasmid, pMD321R3a, containing three units of the desired gene as introduced in tandem. The same procedure was further repeated to give pMD321R5a containing five VIP,Gly genes linked in tandem via Lys-Arg.

(5) Construction of the plasmid pMD500R5

Figure 4:
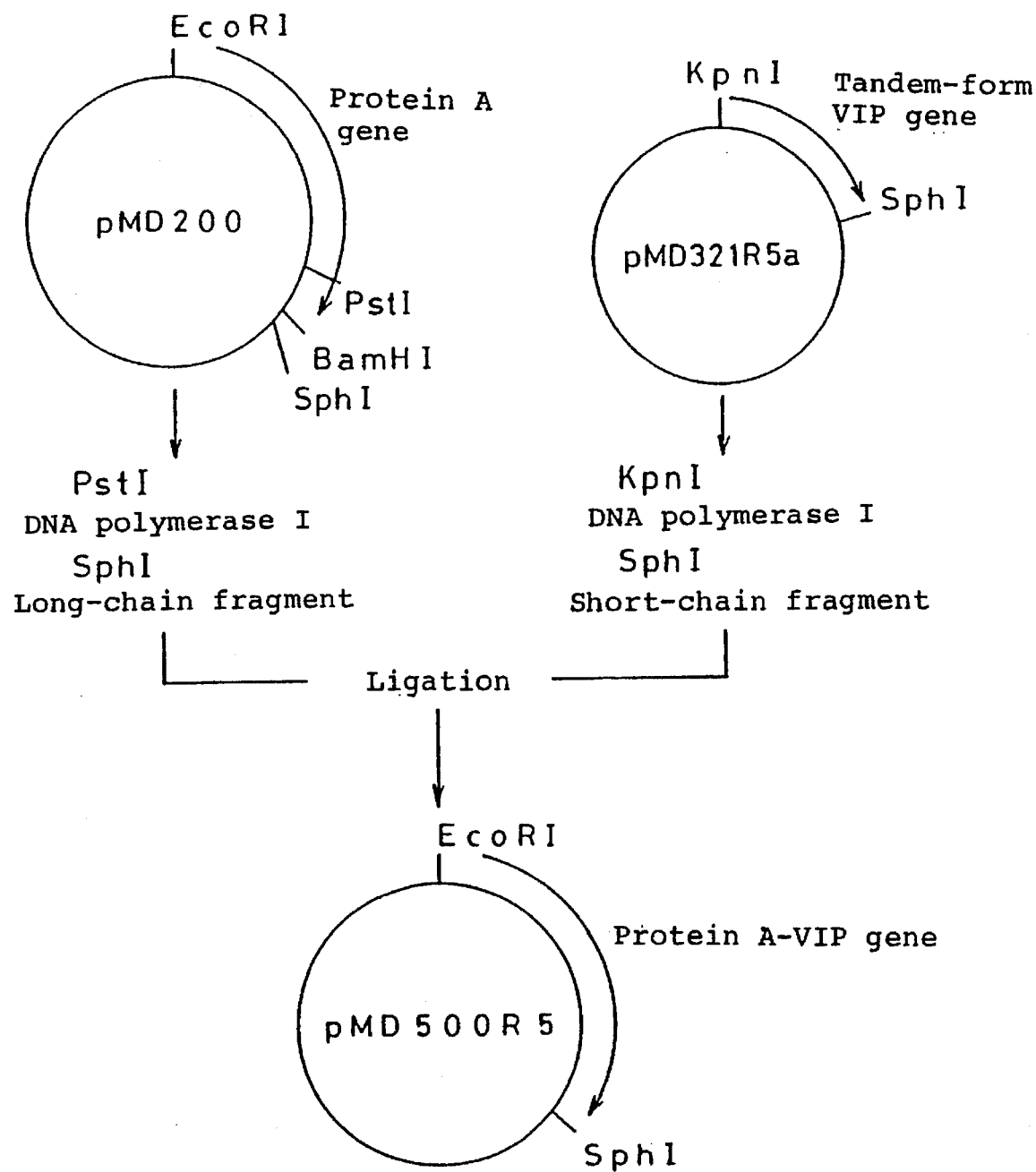
FIG. 4 shows a construction scheme for a plasmid named pMD500R5.

A construction scheme for the plasmid pMD500R5 is shown in FIG. 4. This plasmid secretes a peptide precursor containing 5 molecules of VIP (hereinafter referred to as peptide precursor), with *Bacillus subtilis* as a host.

The above-mentioned plasmid pMD200 was cleaved with the restriction enzyme PstI, rendered blunt-ended using a DNA blunting kit, and further cleaved with the restriction enzyme SphI. A fragment of about 5.5 kb was purified by agarose gel electrophoresis for use as a vector for insertion of a tandem-form VIP gene thereinto.

The tandem-form VIP gene for insertion into said vector was prepared by cleaving the above-mentioned plasmid pMD321R5a with the restriction enzyme KpnI, rendering the resultant fragment blunt-ended using a DNA blunting kit, further cleaving the fragment with the restriction enzyme SphI, and purifying a fragment of about 0.5 kb by polyacrylamide gel electrophoresis. Structurally, this DNA fragment contains the tandem-form VIP gene downstream from genes coding for amino acid sequences recognizable by blood coagulation factor Xa and protein C, respectively. For amidation of VIP, a Gly-encoding gene is linked to the C terminus of each VIP gene. Furthermore, for recovering VIP-Gly from the peptide precursor protein by cleavage, there is the insert sequence Lys-Arg for recognition by PBRS-protease, which is a protease specific to basic amino acid residues, between each neighboring VIP-Gly-encoding genes.

The vector DNA and the tandem-form VIP gene fragment were then ligated to each other using $T_4$ ligase, whereby the peptide precursor protein-secreting plasmid pMD500R5 was constructed.

This plasmid pMD500R5 to which *Bacillis subtilis* serves as a host has a structure such that a region for 5 molecules of VIP-Gly, which is the desired peptide, linked together via Lys-Arg is bound to a carrier region. The carrier is composed of positions 1 to 402 of protein A and a spacer linked thereto, namely Arg-Gly-Ser-Ser-Arg-Val-Asp-Val-Ile-Glu-Gly-Arg-Met-Thr-Ile-Phe-Thr-Phe-Arg (SEQ ID NO: 7), which contains amino acid sequences corresponding to recognition sequences for blood coagulation factor Xa and protein C, respectively.

(6) Production of the fusion protein PAVIPG(P)R5 in the host *Bacillus subtilis* and purification thereof

*Bacillus subtilis* SPL14 (FERM P-10988) was transformed with pMD500R5 by the method of Chang et al. [Chang, S. et al., Mol. Gen. Genet., 168, 111–115 (1979)]. The fusion protein secreted by the thus-obtained transformant Bacillus subtilis SPL14 (pMD500R5) (deposited with the Fermentation Research Institute, Agency of Industrial Science and Technology since Sep. 25, 1990 under the deposit number FERM P-11742) was purified in the following manner.

First, the SPL14 (pMD500R5) strain was shake-cultured in 4 liters of medium A containing 0.5M suc cinic acid at 37° C. for 16 hours. After stopping the cultivation, the protease inhibitors phenylmethylsulfonyl fluoride (PMSF) and EDTA were added to the broth to a concentration of 10 mM, and cells were removed by 30 minutes of centrifugation at 4° C. and 5,000 rpm. The culture supernatant obtained was passed through a 0.22-?m filter, and 3.61 ml of the culture supernatant was applied to a column packed with 300 ml of IgG-Sepharose gel (Pharmacia) at a flow rate of about 6 ml/minute for purifying the fusion protein. The column washed with 2.88 liters of TST buffer [50 mM Tris hydrochloride (pH 7.6), 150 mM NaCl, 0.05% Tween 20] at a flow rate of 4 ml/minute. Elution of the fusion protein was then carried out using 0.1M acetic acid (pH 3.0) at a flow rate of 4 ml/minute. The eluate was immediately neutralized with a half volume of 0.2M ammonium bicarbonate solution. The fusion protein-containing eluate obtained was concentrated using an ultrafiltration filer (cutoff molecular weight 10,000) and then the fusion protein was recovered under the following conditions.

Column: Phenyl-5PWRP, inside diameter 21.5 mm× 15 cm
Rate of flow: 6 ml/min.
Solvents: A: 0.05% Trifluoroacetic acid B: 0.044% Trifluoroacetic acid/60% acetonitrile
Gradient: 27.5 to 30%/50 minutes, 120 ml/ %

The fraction collected was lyophilized to give the desired fusion protein with a molecular weight of 64,000.

The VIP content of the fusion protein was determined by the enzyme immunoassay technique for VIP-Gly as described in the monograph "Koso Men-eki Sokuteiho (Enzyme Immunoassay Techniques)" edited by Eiji Ishikawa et al. and published by Igaku Shoin, as shown below.

First, rabbits were immunized with VIP, and anti-VIP antiserum was obtained. Anti-VIP IgG, anti-VIP F(ab')$_2$ and anti-VIP peroxidase-labeled Fab' were prepared from said anti-VIP antiserum by the maleimide hinge method described in pages 83–92 of the above-cited "Koso Men-eki Sokuteiho".

For assaying VIP-Gly by enzyme immunoassay, the following procedure was followed.

The anti-VIP F(ab')$_2$ was adsorbed on a 96-well ELISA plate, followed by blocking with 1% bovine serum albumin. Test sample solutions were added to this plate and VIP-Gly was allowed to bind to the solid phase-bound anti-VIP F(ab')$_2$. The plate was rinsed, and the anti-VIP peroxidase-labeled Fab$_2$ was further added for sandwiching the solid phase-bound VIP-Gly. After removing the excess free labeled antibody, a reagent solution containing 10 mM orthophenylenediamine (OPD), 0.025% hydrogen peroxide and 50 mM sodium acetate buffer (pH 5.0) was added, and the color produced by reaction with peroxidase was measured in terms of absorption at the wavelength 490 nm.

As a standard reference material, VIP-Gly prepared by solid phase synthesis on an Applied Biosystems (ABI) peptide synthesizer, purified by reversed-phase high-performance liquid chromatography and confirmatively checked on its amino acid composition was used.

As a result, the secretory production of the desired fusion protein was verified. The yield of the fusion protein from the 4-liter broth was about 37 mg as calculated based on the absorption at the wavelength 214 nm of a peak revealed to be VIP-active in ELISA.

The structure of the fusion protein PAVIPG(P)R5 is schematically shown below. Each desired peptide (VIP-Gly) is indicated by a double underline, and the recognition sites for factor Xa, kallikrein or basic amino acid residue pair-specific protease are each indicated by a single underline.
Protein A(1–402 )-ArgGlySerSerArgValAspVal-IleGluGly-Arg-MetThrIlePheThr-PheArg-VIP-Gly-LysArg-VIP-Gly-LysArg-VIP-Gly-Lys-Arg-VIP-Gly-Lys-Arg-VIP-Gly
(SEQ ID NO: 18)

(7) Excision of VIP-Gly and VIP-Gly-Lys-Arg from the fusion protein PAVIPG(P)R5

Figure 5:
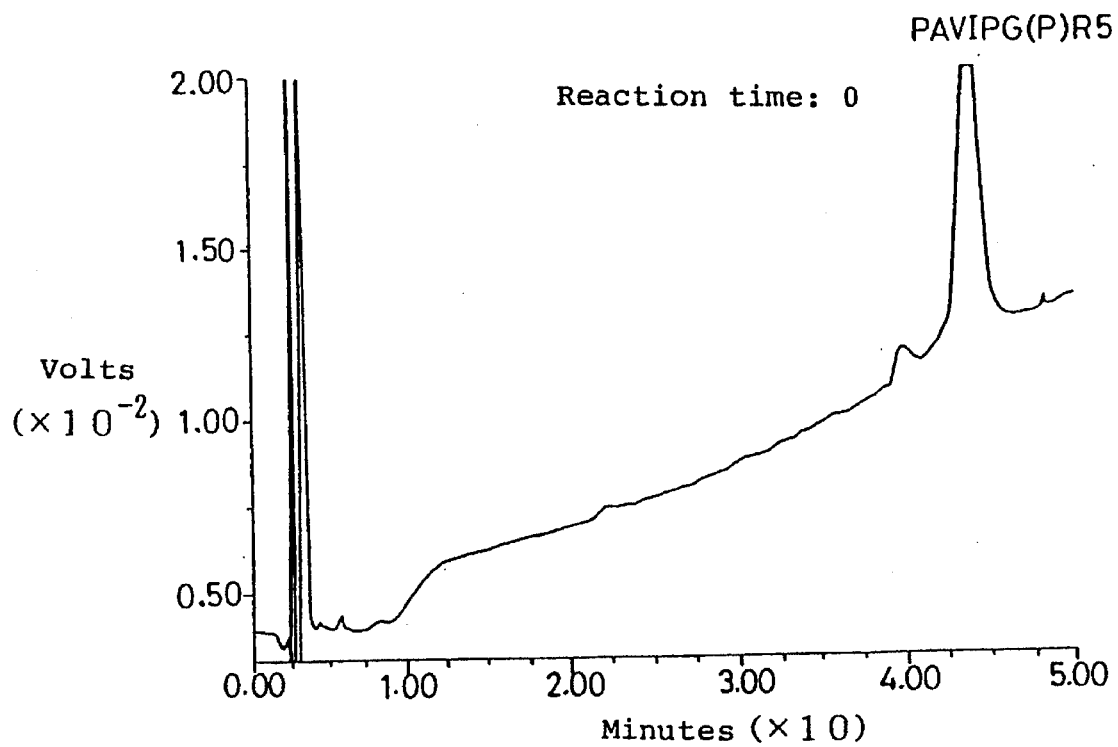
FIG. 5 (A) and (B) each shows a chromatogram illustrating the elution pattern in reversed-phase high-performance liquid chromatography of a reaction mixture prepared or obtained in Example 1.
Figure 5:
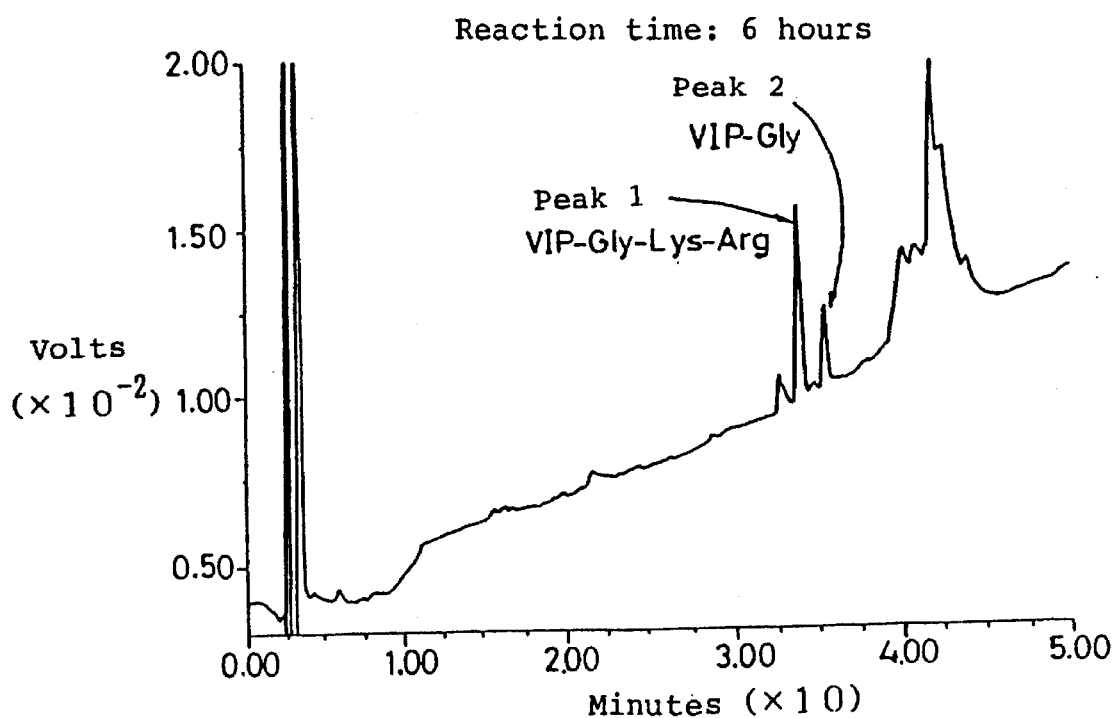

A 100-µg portion of the fusion protein (1.55 nano moles) was treated with 0.05 mU of the basic amino acid residue pair-specific protease purified in the abovementioned step (1) (Benz-I fraction) [1 U of said protease being defined as the activity liberating 1 micromole of AMC per minute when the enzyme is reacted with 0.1 mM Boc-Gln-Arg-Arg-MCA (Boc=t-butoxycarbonyl, MCA=4-methylcoumaryl-7-amide) in 50 mM Tris hydrochloride (pH 7.0) containing 0.1% Lubrol PX and 0.5 mM $CaCl_2$ at 30° C.] in 50 mM Tris hydrochloride (pH 7.0) containing 1 mM $CaCl_2$ at 37° C. Chromatograms obtained in reversed-phase high-performance chromatography at reaction times 0 and 6 hours are shown in FIG. 5 (A) and (B). With the progress of the cleavage reaction, peaks 1 and 2 appeared as main new peaks. These peaks 1 and 2 were isolated by reversed phase high-performance chromatography and analyzed for their amino acid sequences using a protein sequencer. Peak 1 was quite identical with VIP-Gly-Lys-Arg (SEQ ID NO: 5), and peak 2 with VIP-Gly (SEQ ID NO: 2).

Example 2

Excision of VIP-Gly (SEQ ID NO: 2) from the fusion protein PAVIPG(P)R5

Figure 6:
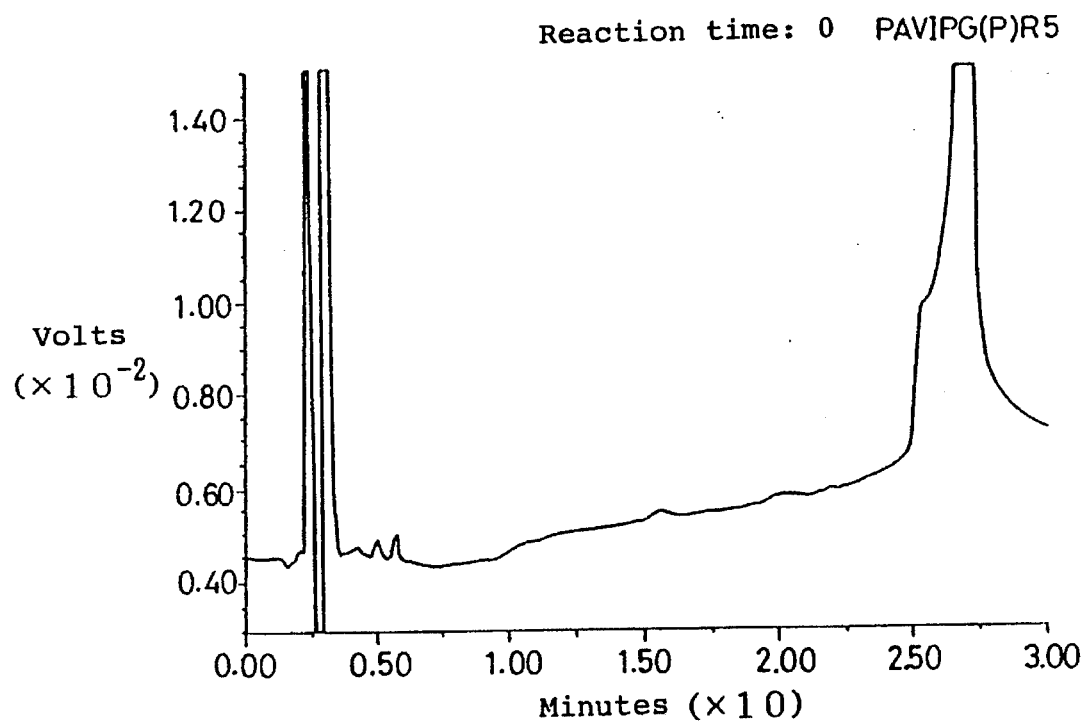
FIG. 6 (A) and (B) each shows a chromatogram illustrating the elution pattern in reversed-phase high-performance liquid chromatography of a reaction mixture prepared or obtained in Example 2.
Figure 6:
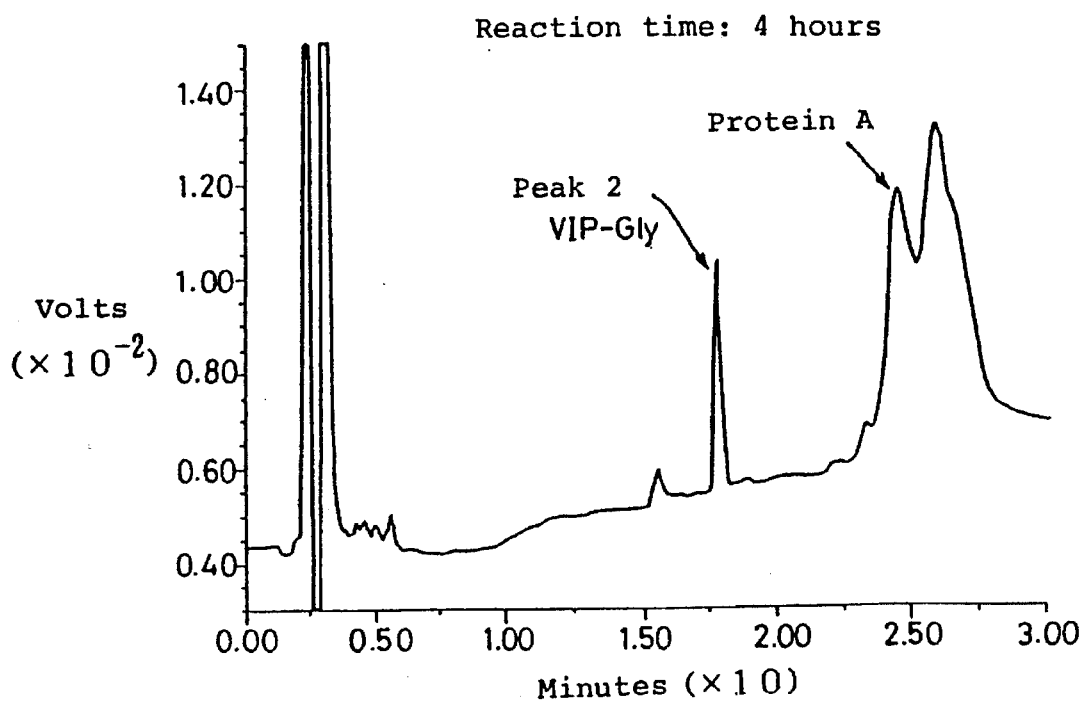

A 100-µg portion of the fusion protein (1.55 nano moles) was treated with 0.1 mU of the basic amino acid residue pair-specific protease (Benz-I fraction) purified in step (1) in Example 1 (1 U being defined as above) and 50 mU of carboxypeptidase B (Sigma Chemical) [1 U being defined as the enzyme activity liberating 1 micromole of Arg per minute when the enzyme is reacted with 1 mM Bz-Gly-Arg (Bz=benzyloxycarbonyl) in 25 mM Tris hydrochloride (pH 8.0) at 25° C.] in 50 mM Tris hydrochloride (pH 7.0) containing 1 mM $CaCl_2$ at 37° C. Chromatograms obtained by reversed-phase high-performance chromatography at reaction times 0 and 4 hours are shown in FIG. 6 (A) and (B). With the progress of the cleavage reaction, one peak appeared as a main one. This peak was identical with that identified as VIP-Gly (SEQ ID NO: 2) in Example 1. The appearance of VIP-Gly-Lys-Arg (SEQ ID NO: 5) was little.

Comparative Example 1

Partial digestion of the fusion protein PAVIPG(P)R5 with blood coagulation factor Xa 100 µg of the fusion protein PAVIPG(P)R5 was treated with 15.5 picomoles of blood coagulation factor Xa (Boehringer Mannheim-Yamanouchi) in 50 mM Tris hydrochloride (pH 8.0) containing 1 mM $CaCl_2$ and 0.1M NaCl. The cleavage reaction occurred not only on the desired C-terminal side of Ile-Glu-Gly-Arg (SEQ ID NO: 20) but also between $Arg^{14}$-Lys in the middle of VIP, so that the desired protein [Met-Thr-Ile-Phe-Thr-Phe-Arg-(VIP-Gly)4-VIP-Gly] (SEQ ID NO: 18) could not be obtained.

Comparative Example 2

Partial digestion of the fusion protein PAVIPG(P)R5 with kallikrein

100 µg of the fusion protein PAVIPG(P)R5 was treated with 15.5 picomoles of kallikrein (from human serum; Sigma Chemical) in 50 mM Tris hydrochloride (pH 8.0) containing 1 mM $CaCl_2$ and 0.1M NaCl. The cleavage reaction occurred between $Arg^{14}$-Lys within VIP as well and further within VIP-Gly-(14–29), so that the desired protein [(VIP-Gly-Lys-Arg)4-VIP-Gly] (SEQ ID NO: 24) could not be obtained.

We claim:

1. A method of producing a peptide or a protein, wherein said method comprises expressing a recombinant DNA in a host microorganism, said DNA encoding a fusion protein represented by the formula $$A\text{-}B\text{-}C \qquad (Ia)$$

or $$C\text{-}B\text{-}A \qquad (Ib)$$

wherein A represents a carrier, B represents an enzymatically excisable dipeptide of the formula $X_1$–$X_2$ (in which $X_1$ is Lys, Arg or Pro bound to the C-terminus of A in the case of (Ia) and to the C-terminus of C in the case of (Ib), and $X_2$ is Lys or Arg bound to the N-terminus of C in the case of (Ia) and to the N-terminus of A in the case of (Ib) provided that when $X_1$ is Pro, $X_2$ is Arg, which does not occur in a desired peptide or protein, and C represents the desired peptide or protein, said host microorganism being a mutant strain showing low protease productivity derived from a parent *Bacillus subtilis* strain by introduction of a spoOAΔ677 mutant gene, wherein said parent *Bacillus subtilis* lacks an ability to produce either alkaline protease or neutral protease and shows a protease activity of not more than about 3% as compared to wild strains, and treating said fusion protein at least with a protease capable of specifically recognizing said dipeptide represented by B and specifically hydrolyzing a peptide bond of said dipeptide.

2. The method of producing a peptide or a protein as claimed in claim 1, wherein the carrier is the whole or part of α-amylase, neutral or alkaline protease, cellulase, β-lactamase, β-galactosidase, chloramphenicol acetyl transferase, RecA protein, trpE, human interleukin-2, human growth hormone, dihydrofolate reductase, protein A, λ-cII, alkaline phosphatase, penicillinase or the like, or a derivative thereof, which can be produced by the host microorganism intracellularly or extracellularly or in the periplasm.

3. The method of producing a peptide or a protein as claimed in claim 2, wherein the carrier is *Staphylococcus aureus*-derived protein A.

4. The method of producing a peptide or a protein as claimed in claim 1, wherein the desired peptide or protein is a physiologically active peptide selected from the group consisting of insulin, gastrin, opioid peptides, epithelial growth factor, endothelin, vasoactive intestinal polypeptide (VIP), atrial natriuretic peptide, substance P, calcitonin, insulin-like growth factors I and II, galanin, motilin and vasopressin; a protein selected from the group consisting of hirudin, eglin C, secretory leukocyte-derived protease inhibitor, human albumin, blood coagulation factors, lymphokines, nerve growth factor and liver cell regeneration factor; or a precursor of said peptide or protein.

5. The method of producing a peptide or a protein as claimed in claim 4, wherein said peptide is a VIP precursor having the amino acid sequence H—His—Ser—Asp—Ala—Val—Phe—Thr—Asp—Asn—Tyr—Thr—Arg—Leu—
Arg—Lys—Gln—Met—Ala—Val—Lys—Lys—Tyr—Leu—Asn—Ser—Ile—Leu—
Asn—Gly—X wherein X is OH (SEQ ID NO: 2), Lys-OH (SEQ ID NO: 3), Arg-OH (SEQ ID NO: 4), Lys-Arg-OH (SEQ ID NO: 5) or Arg-Lys-OH (SEQ ID NO: 6).

6. The method of producing a peptide or a protein as claimed in claim 1, wherein the dipeptide is Lys-Arg or Arg-Arg.

7. The method of producing a peptide or a protein as claimed in claim 1, wherein the fusion protein is treated with a protease together with an aminopeptidase specifically releasing a basic amino acid from the N terminus of the dipeptide chain and/or a carboxypeptidase specifically releasing a basic amino acid from the C terminus of the dipeptide chain.

8. The method of producing a peptide or a protein as claimed in claim 7, wherein the aminopeptidase is aminopeptidase B (E. C. 3.4.11.6).

9. The method of producing a peptide or a protein as claimed in claim 7, wherein the carboxypeptidase includes at least one member of the group consisting of carboxypeptidase B (E.C. 3.4.17.2), carboxypeptidase E (enkephalin convertase), carboxypeptidase N (E.C. 3.4. 17.3) and yscα.

10. The method of producing a peptide or a protein as claimed in claim 1, wherein the fusion protein is treated with the protease at a pH of about 6 to about 10 and a temperature of about 15° C. to about 60° C.

11. The method of producing a peptide or a protein as claimed in claim 1, wherein each micromole of the fusion protein is treated with about 0.001 to about 100 U of the protease.

12. The method of producing a peptide or a protein as claimed in claim 1, wherein the mutant strain showing low protease activity derived from a *Bacillus subtilis* strain is *Bacillus subtilis* SPO11 derived from *Bacillus subtilis* 104HL by introduction of the spoOAΔ677 mutant gene.

13. The method of producing a peptide or a protein as claimed in claim 1, wherein the mutant strain showing low protease productivity derived from a *Bacillus subtilis* strain is *Bacillus subtilis* SPL14 derived from *Bacillus subtilis* DY-16 by introduction of the spoOAΔ677 mutant gene.

14. A method of producing a peptide or protein, wherein said method comprises expressing a recombinant DNA in a host microorganism, said DNA encoding a tandem-form fusion protein containing at least one unit represented by the formula $$(B\text{-}C)_n \qquad (II)$$

or $$(C\text{-}B)_n \qquad (III)$$

wherein B represents an enzymatically excisable dipeptide of the formula $$X_1\text{-}X_2$$

in which $X_1$ is Lys, Arg or Pro and $X_2$ is Lys or Arg, provided that when $X_1$ is Pro, $X_2$ is Arg, which does not occur in a desired peptide or protein, C represents the desired peptide or protein, and n is an integer of 2 or more, said host microorganism being a mutant strain showing low protease productivity derived from a parent *Bacillus subtilis* strain by introduction of a spoOAΔ677 mutant gene, where said parent Bacillus subtilis strain lacks an ability to produce either alkaline protease or neutral protease and shows a protease activity of not more than about 3% as compared with wild strains and treating said fusion protein at least with a protease capable of specifically recognizing said dipeptide and specifically hydrolyzing the peptide bond of said dipeptide.

15. The method of producing a peptide or a protein claimed in claim 14, wherein the tandem-form fusion protein containing the unit [II] or [III] is represented by the formula $$A\text{-}(B\text{---}C)_{\overline{n}} \quad [\text{IIa}]$$

$$C\text{-}(B\text{---}C)_{\overline{n}}B\text{---}A \quad [\text{IIb}]$$

$$C\text{-}(B\text{---}C)_{\overline{n}}A \quad [\text{IIc}]$$

$$(C\text{---}B)_{\overline{n}}A \quad [\text{IIIa}]$$

$$A\text{---}B\text{-}(C\text{---}B)_{\overline{n}}C \quad [\text{IIIb}]$$

or $$A\text{-}(C\text{---}B)_{\overline{n}}C \quad [\text{IIIc}]$$

wherein A stands for a carrier.

16. The method of producing a peptide or a protein as claimed in claim 15, wherein n is 2 to 20.

17. The method for producing a peptide or a protein as claimed in claim 14, wherein the desired peptide or protein is a physiologically active peptide selected from the group consisting of insulin, gastrin, opioid peptides, epithelial growth factor, endothelin, vasoactive intestinal polypeptide (VIP), atrial natriuretic peptide, substance P, calcitonin, insulin-like growth factors I and II, galanin, motilin and vasopressin; a protein selected from the group consisting of hirudin, eglin C, secretory leukocyte-derived protease inhibitor, human albumin, blood coagulation factors, lymphokines, nerve growth factor and liver cell regeneration factor; or a precursor of said peptide or protein.

18. The method of producing a peptide or a protein as claimed in claim 14, wherein the dipeptide is Lys-Arg or Arg-Arg.

19. The method of producing a peptide or a protein as claimed in claim 14, wherein the fusion protein is treated with a protease together with an aminopeptidase specifically releasing a basic amino acid from the N terminus of the dipeptide chain and/or a carboxypeptidase specifically releasing a basic amino acid from the C terminus of the dipeptide chain.

20. The method of producing a peptide or a protein as claimed in claim 14, wherein the protease includes at least one protease capable of specifically hydrolyzing the peptide bond on the C-terminal side of the dipeptide chain as selected from the group consisting of IRCM serine protease I, POMC converting enzyme, and proteases derived respectively from strains of the genera Saccharomyces, Kluyveromyces, Sporobolomyces, Filobasidium, Hansenula, Issatchenkia, Pichia, Rhodosporidium and Saccharomycopsis.

21. The method of producing a peptide or a protein as claimed in claim 14, wherein the host microorganism is a yeast, a fungus, or a microorganism belonging to the genus Escherichia, Bacillus or Staphylococcus.

22. The method of producing a peptide or a protein as claimed in claim 14, wherein the fusion protein is treated with the protease at a pH of about 6 to about 10 and a temperature of about 15° C. to about 60° C.

23. The method of producing a peptide or a protein as claimed in claim 14, wherein each micromole of the fusion protein is treated with about 0.001 to about 100 U of the protease.

24. The method of producing a peptide or a protein as claimed in claim 14, wherein the mutant strain showing low protease activity derived from a *Bacillus subtilis* strain is *Bacillus subtilis* SPO11 derived from *Bacillus subtilis* 104HL by introduction of the spoOAΔ677 mutant gene.

25. The method of producing a peptide or a protein as claimed in claim 14, wherein the mutant strain showing low protease productivity derived from a Bacillus subtilis strain is *Bacillus subtilis* SPL14 derived from *Bacillus subtilis* DY-16 by introduction of the spoOAΔ677 mutant gene.

\* \* \* \* \*

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

His  Ser  Asp  Ala  Val  Phe  Thr  Asp  Asn  Tyr  Thr  Arg  Leu  Arg  Lys  Gln
        1                       5                                  10                          15

Met  Ala  Val  Lys  Lys  Tyr  Leu  Asn  Ser  Ile  Leu  Asn
                        20                                  25

( 2 ) INFORMATION FOR SEQ ID NO:2:

( i ) SEQUENCE CHARACTERISTICS:
        ( A ) LENGTH: 29 amino acids
        ( B ) TYPE: amino acid (D) TOPOLOGY: linear (ii) MOLECULE TYPE: peptide (xi) SEQUENCE DESCRIPTION: SEQ ID NO:2:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly
            20                  25

(2) INFORMATION FOR SEQ ID NO:3:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: <1
        (D) OTHER INFORMATION: /note="Xaa=K-OH"

(xi) SEQUENCE DESCRIPTION: SEQ ID NO:3:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Lys
            20                  25                  30

(2) INFORMATION FOR SEQ ID NO:4:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:4:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Arg
            20                  25                  30

(2) INFORMATION FOR SEQ ID NO:5:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:5:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Lys Arg
            20                  25                  30

(2) INFORMATION FOR SEQ ID NO:6:

(i) SEQUENCE CHARACTERISTICS:
        (A) LENGTH: 31 amino acids
        (B) TYPE: amino acid
        (D) TOPOLOGY: linear (ii) MOLECULE TYPE: peptide ( x i ) SEQUENCE DESCRIPTION: SEQ ID NO:6:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Arg Lys
        20                  25                  30

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Arg Gly Ser Ser Arg Val Asp Val Ile Glu Gly Arg Met Thr Ile Phe
1               5                   10                  15

Thr Phe Arg ( 2 ) INFORMATION FOR SEQ ID NO:8:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TCTAGAGTCG ACGTCATTGA AGGAAGAATG ACAATTTTTA CATTCAGGCA TAGCGACG    58

( 2 ) INFORMATION FOR SEQ ID NO:9:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GCGTCGCTAT GCCTGAATGT AAAAATTGTC ATTCTTCCTT CAATGACGTC GACTC    55

( 2 ) INFORMATION FOR SEQ ID NO:10:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CAGTCTTCAC AGATAACTAC ACGCGTTTAA GAAAGCAAAT GGCTGTG    47

( 2 ) INFORMATION FOR SEQ ID NO:11:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CCATTTGCTT TCTTAAACGC GTGTAGTTAT CTCTGAAGAC T    41

( 2 ) INFORMATION FOR SEQ ID NO:12:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

AAAAAATATT TGAATTCTAT TCTTAACGGC TAATAGATCT AAAAAGAAGC AGG    53

( 2 ) INFORMATION FOR SEQ ID NO:13:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

TTCTTTTTAG ATCTATTAGC CGTTAAGAAT AGAATTCAAA TATTTTTTCA CAG    53

( 2 ) INFORMATION FOR SEQ ID NO:14:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TTCCTCCATA CCTGCTTCTT TTTATTTGTC AGCATCCTGA TGTTGGATCC GCATG    55

( 2 ) INFORMATION FOR SEQ ID NO:15:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

```
CGGATCCAAC ATCAGGATGC TGACAAATAA AAAGAAGCAG GTATGGAGGA ACCTGC        56
```

( 2 ) INFORMATION FOR SEQ ID NO:16:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3..161

( x i ) SEQUENCE DESCRIPTION: SEQ ID NO:16:

```
AA TTC GAG CTC GGT ACC CGG GGA TCC TCT AGA GTC GAC GTC ATT GAA         47
   Phe Glu Leu Gly Thr Arg Gly Ser Ser Arg Val Asp Val Ile Glu
   1               5                   10                  15

GGA AGA ATG ACA ATT TTT ACA TTC AGG CAT AGC GAC GCA GTC TTC ACA        95
Gly Arg Met Thr Ile Phe Thr Phe Arg His Ser Asp Ala Val Phe Thr
                20                  25                  30

GAT AAC TAC ACG CGT TTA AGA AAG CAA ATG GCT GTG AAA AAA TAT TTG       143
Asp Asn Tyr Thr Arg Leu Arg Lys Gln Met Ala Val Lys Lys Tyr Leu
            35                  40                  45

AAT TCT ATT CTT AAC GGC TAATAGATCT AAAAAGAAGC AGGTTCCTCC              191
Asn Ser Ile Leu Asn Gly
            50

ATACCTGCTT CTTTTTATTT GTCAGCATCC TGATGTTGGA TCCGCATGCA AGCTTGGCAC     251

TGGCCGTCGT TTTACAACGT CGTGACTGGG AAAACCCTGG CGTTACCCA                 300
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
Pro Xaa Gly Pro
1
```

( 2 ) INFORMATION FOR SEQ ID NO:18:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: <1
        ( D ) OTHER INFORMATION: /note="Protein A(1-402)"

( x i ) SEQUENCE DESCRIPTION: SEQ ID NO:18:

```
Arg Gly Ser Ser Arg Val Asp Val Ile Glu Gly Arg Met Thr Ile Phe
 1               5                  10                  15

Thr Phe Arg His Ser Asp Ala Val Phe Thr Asp Asn Tyr Thr Arg Leu
            20                  25                  30

Arg Lys Gln Met Ala Val Lys Lys Tyr Leu Asn Ser Ile Leu Asn Gly
        35                  40                  45

Lys Arg His Ser Asp Ala Val Phe Thr Asp Asn Tyr Thr Arg Leu Arg
    50                  55                  60

Lys Gln Met Ala Val Lys Lys Tyr Leu Asn Ser Ile Leu Asn Gly Lys
65                  70                  75                  80

Arg His Ser Asp Ala Val Phe Thr Asp Asn Tyr Thr Arg Leu Arg Lys
                85                  90                  95

Gln Met Ala Val Lys Lys Tyr Leu Asn Ser Ile Leu Asn Gly Lys Arg
            100                 105                 110

His Ser Asp Ala Val Phe Thr Asp Asn Tyr Thr Arg Leu Arg Lys Gln
        115                 120                 125

Met Ala Val Lys Lys Tyr Leu Asn Ser Ile Leu Asn Gly Lys Arg His
    130                 135                 140

Ser Asp Ala Val Phe Thr Asp Asn Tyr Thr Arg Leu Arg Lys Gln Met
145                 150                 155                 160

Ala Val Lys Lys Tyr Leu Asn Ser Ile Leu Asn Gly
                165                 170
```

( 2 ) INFORMATION FOR SEQ ID NO:19:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Met Thr Ile Phe Thr Phe Arg His Ser Asp Ala Val Phe Thr Asp Asn
 1               5                  10                  15

Tyr Thr Arg Leu Arg Lys Gln Met Ala Val Lys Lys Tyr Leu Asn Ser
            20                  25                  30

Ile Leu Asn Gly His Ser Asp Ala Val Phe Thr Asp Asn Tyr Thr Arg
        35                  40                  45

Leu Arg Lys Gln Met Ala Val Lys Lys Tyr Leu Asn Ser Ile Leu Asn
    50                  55                  60

Gly His Ser Asp Ala Val Phe Thr Asp Asn Tyr Thr Arg Leu Arg Lys
65                  70                  75                  80
```

```
        Gln  Met  Ala  Val  Lys  Lys  Tyr  Leu  Asn  Ser  Ile  Leu  Asn  Gly  His  Ser
                            85                      90                          95

Asp  Ala  Val  Phe  Thr  Asp  Asn  Tyr  Thr  Arg  Leu  Arg  Lys  Gln  Met  Ala
                       100                     105                      110

Val  Lys  Lys  Tyr  Leu  Asn  Ser  Ile  Leu  Asn  Gly  His  Ser  Asp  Ala  Val
                  115                      120                      125

Phe  Thr  Asp  Asn  Tyr  Thr  Arg  Leu  Arg  Lys  Gln  Met  Ala  Val  Lys  Lys
             130                     135                      140

Tyr  Leu  Asn  Ser  Ile  Leu  Asn  Gly
        145                 150
```

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
        Ile  Glu  Gly  Arg
        1
```

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
        Val  Asp  Asp  Asp  Asp  Lys
        1                   5
```

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
        Pro  Phe  His  Leu  Leu  Val  Tyr
        1                   5
```

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
        Lys  Ser  Ser  Lys
        1
```

( 2 ) INFORMATION FOR SEQ ID NO:24:

( i ) SEQUENCE CHARACTERISTICS:
        ( A ) LENGTH: 152 amino acids (B) TYPE: amino acid
(D) TOPOLOGY: linear (ii) MOLECULE TYPE: peptide (xi) SEQUENCE DESCRIPTION: SEQ ID NO:24:

| His | Ser | Asp | Ala | Val | Phe | Thr | Asp | Asn | Tyr | Thr | Arg | Leu | Arg | Lys | Gln |
|---|---|---|---|---|---|---|---|---|---|---|---|---|---|---|---|
| 1 | | | | 5 | | | | | 10 | | | | | 15 | |

| Met | Ala | Lys | Lys | Tyr | Leu | Asn | Ser | Ile | Leu | Asn | Gly | Lys | Arg | His | Ser |
|---|---|---|---|---|---|---|---|---|---|---|---|---|---|---|---|
| | | | 20 | | | | | 25 | | | | | 30 | | |

| Asp | Ala | Val | Phe | Thr | Asp | Asn | Tyr | Thr | Arg | Leu | Arg | Lys | Gln | Met | Ala |
|---|---|---|---|---|---|---|---|---|---|---|---|---|---|---|---|
| | | | 35 | | | | 40 | | | | | 45 | | | |

| Val | Lys | Lys | Tyr | Leu | Asn | Ser | Ile | Leu | Asn | Gly | Lys | Arg | His | Ser | Asp |
|---|---|---|---|---|---|---|---|---|---|---|---|---|---|---|---|
| | 50 | | | | | 55 | | | | | 60 | | | | |

| Ala | Val | Phe | Thr | Asp | Asn | Tyr | Thr | Arg | Leu | Arg | Lys | Gln | Met | Ala | Val |
|---|---|---|---|---|---|---|---|---|---|---|---|---|---|---|---|
| 65 | | | | | 70 | | | | | 75 | | | | | 80 |

| Lys | Lys | Tyr | Leu | Asn | Ser | Ile | Leu | Asn | Gly | Lys | Arg | His | Ser | Asp | Ala |
|---|---|---|---|---|---|---|---|---|---|---|---|---|---|---|---|
| | | | | 85 | | | | | 90 | | | | | 95 | |

| Val | Phe | Thr | Asp | Asn | Tyr | Thr | Arg | Leu | Arg | Lys | Gln | Met | Ala | Val | Lys |
|---|---|---|---|---|---|---|---|---|---|---|---|---|---|---|---|
| | | | 100 | | | | | 105 | | | | | 110 | | |

| Lys | Tyr | Leu | Asn | Ser | Ile | Leu | Asn | Gly | Lys | Arg | His | Ser | Asp | Ala | Val |
|---|---|---|---|---|---|---|---|---|---|---|---|---|---|---|---|
| | | | 115 | | | | | 120 | | | | | 125 | | |

| Phe | Thr | Asp | Asn | Tyr | Thr | Arg | Leu | Arg | Lys | Gln | Met | Ala | Val | Lys | Lys |
|---|---|---|---|---|---|---|---|---|---|---|---|---|---|---|---|
| | 130 | | | | | 135 | | | | | 140 | | | | |

| Tyr | Leu | Asn | Ser | Ile | Leu | Asn | Gly |
|---|---|---|---|---|---|---|---|
| 145 | | | | | 150 | | |

(2) INFORMATION FOR SEQ ID NO:25:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:25:

| Thr | Ile | Phe | Thr | Phe | Arg |
|---|---|---|---|---|---|
| 1 | | | | 5 | |

(2) INFORMATION FOR SEQ ID NO:26:

(i) SEQUENCE CHARACTERISTICS:
(A) LENGTH: 53 amino acids
(B) TYPE: amino acid
(D) TOPOLOGY: linear (ii) MOLECULE TYPE: peptide (xi) SEQUENCE DESCRIPTION: SEQ ID NO:26:

| Phe | Glu | Leu | Gly | Thr | Arg | Gly | Ser | Ser | Arg | Val | Asp | Val | Ile | Glu | Gly |
|---|---|---|---|---|---|---|---|---|---|---|---|---|---|---|---|
| 1 | | | | 5 | | | | | 10 | | | | | 15 | |

| Arg | Met | Thr | Ile | Phe | Thr | Phe | Arg | His | Ser | Asp | Ala | Val | Phe | Thr | Asp |
|---|---|---|---|---|---|---|---|---|---|---|---|---|---|---|---|
| | | | 20 | | | | | 25 | | | | | 30 | | |

| Asn | Tyr | Thr | Arg | Leu | Arg | Lys | Gln | Met | Ala | Val | Lys | Lys | Tyr | Leu | Asn |
|---|---|---|---|---|---|---|---|---|---|---|---|---|---|---|---|
| | | 35 | | | | | 40 | | | | | 45 | | | |

| Ser | Ile | Leu | Asn | Gly |
|---|---|---|---|---|
| | 50 | | | |